US008674125B2

(12) United States Patent
Taillefer et al.

(10) Patent No.: US 8,674,125 B2
(45) Date of Patent: Mar. 18, 2014

(54) METHOD FOR THE PREPARATION OF PHOSPHINE BUTADIENE LIGANDS, COMPLEXES THEREOF WITH COPPER AND USE THEREOF IN CATALYSIS

(71) Applicants: Centre National de la Recherche Scientifique (C.N.R.S.), Paris (FR); Ecole Nationale Superieure de Chimie de Montpellier, Montpellier (FR); Universite Sidi Mohammed Ben Abdellah, Fes (MA)

(72) Inventors: Marc Taillefer, Vailhauques (FR); Hamid Kaddouri, Montpellier (FR); Fouad Ouazzani, Fes (MA); Armelle Ouali, Toulouse (FR)

(73) Assignees: Centre National de la Recherche Scientifique (C.N.R.S.), Paris (FR); Ecole Nationale Superieure de Chimie de Montpellier, Montpellier (FR); Universite Sidi Mohammed Ben Abdellah, Fes (MA)

( * ) Notice: Subject to any disclaimer, the term of this patent is extended or adjusted under 35 U.S.C. 154(b) by 0 days.

(21) Appl. No.: 13/777,799

(22) Filed: Feb. 26, 2013

(65) Prior Publication Data
US 2013/0165667 A1  Jun. 27, 2013

Related U.S. Application Data

(62) Division of application No. 12/450,940, filed as application No. PCT/IB2008/000984 on Apr. 21, 2008, now abandoned.

(30) Foreign Application Priority Data

Apr. 20, 2007  (FR) .................................. 07 02878

(51) Int. Cl.
*C07F 9/28* (2006.01)
(52) U.S. Cl.
USPC .................................. 556/21; 556/19; 568/8
(58) Field of Classification Search
USPC ........................................ 556/21, 19; 568/8
See application file for complete search history.

(56) References Cited

U.S. PATENT DOCUMENTS

| 5,710,339 | A | * | 1/1998 | Laue et al. ................... 568/16 |
| 6,867,298 | B2 | | 3/2005 | Buchwald et al. |
| 6,894,191 | B1 | * | 5/2005 | Kelkar et al. ................ 564/405 |
| 2002/0128519 | A1 | | 9/2002 | Ernst et al. |
| 2003/0171593 | A1 | | 9/2003 | Cellier et al. |
| 2003/0236413 | A1 | | 12/2003 | Cellier et al. |
| 2004/0147390 | A1 | | 7/2004 | Schanen et al. |
| 2005/0065350 | A1 | | 3/2005 | Taillefer et al. |
| 2005/0234239 | A1 | | 10/2005 | Taillefer et al. |
| 2006/0106257 | A1 | | 5/2006 | Ernst et al. |
| 2006/0264673 | A1 | | 11/2006 | Buchwald et al. |
| 2007/0225524 | A1 | | 9/2007 | Schanen et al. |
| 2008/0194886 | A1 | | 8/2008 | Schanen et al. |
| 2009/0240061 | A1 | | 9/2009 | Spindler et al. |

FOREIGN PATENT DOCUMENTS

| EP | 1 241 157 A1 | 9/2002 |
| FR | 2 838 441 A1 | 10/2003 |
| WO | WO 03/101966 A1 | 12/2003 |
| WO | WO 2004/048323 A1 | 6/2004 |

OTHER PUBLICATIONS

Cabioch et al., "Preparative synthesis of primary vinylphosphines by chemoselective reduction of the corresponding vinylphosphonates," *Journal of Organometallic Chemistry*, vol. 377, 1989, pp. 227-233.
Abstract of Ullmann et al., *Berichte des Deutschen Chemischen Gesellschaft*, vol. 38, 1905, pp. 2120-2126.
Teulade et al., "A General One-Pot Synthesis of 1,3-Butadienyl Phosphanes," *Tetrahedron Letters*, vol. 30, No. 46, 1989, pp. 6327-6330.
Fryzuk et al., "Transition Metal Dienyls in Organic Synthesis. Dienyl Transfer Reactions from Zirconium to Phosphorus and to Boron," *J. Org. Chem.*, vol. 53, 1988, pp. 4425-4426.
Xi et al., "Selective preparation of 1,3-butadienyl phosphines, 1-iodo- and 1,4-diiodo-butadienyl phosphine oxides via zirconocene-mediated cross-coupling of alkynylphosphines," *Tetrahedron Letters*, vol. 45, 2004, pp. 2427-2429.
Patil et al., "Novel CuI/tributyl phosphine catalyst system for amination of aryl chlorides," *Chem. Commun.*, 2003, pp. 2460-2461.
Macomber et al., "($\eta^5$-Cyclopentadienyl)- and ($\eta^5$Pentamethylcyclopentadienyl)copper Compounds Containing Phosphine, Carbonyl, and $\eta^2$-Acetylenic Ligands," *J. Am. Chem. Soc.*, vol. 105, 1983, pp. 5325-5329.
Mathey et al., "1,3-Butadienylphosphines and Some of Their Complexes," *Inorg. Chem.*, vol. 19, 1980, pp. 1813-1816.
Di Nicola et al., "Synthesis, spectroscopic and structural characterization of adducts of stoichiometry CuX:dppe (1:2) (X=I, ClO$_4$, BH$_4$, O$_3$SCF$_3$, SCN, dppe = Ph$_2$P(CH$_2$)$_2$PPh$_2$)," *Inorganica Chimica Acta*, vol. 358, 2005, pp. 4003-4008.
Divanidis et al., "Linking thione-ligated copper(I) centres with *trans*-1,2-bis(diphenylphosphino)ethane (*trans*-dppen): crystal structures of the pyrimidine-2-thione derivatives [CuBr($\mu_2$-*trans*-dppen)pymtH)]$_2$ and [CuI($\mu_2$-*trans*-dppen)pymtH)]$_2$," *Polyhedron*, vol. 24, 2005, pp. 351-358.

(Continued)

*Primary Examiner* — Johann R Richter
*Assistant Examiner* — Pancham Bakshi
(74) *Attorney, Agent, or Firm* — Oliff PLC

(57) ABSTRACT

A method for the creation of a carbon-carbon (C—C) bond or of a carbon-heteroatom (C-HE) bond includes reacting a compound carrying a leaving group with a nucleophilic compound carrying a carbon atom or a heteroatom (HE) capable of replacing the leaving group, thus creating a C—C or C-HE bond, in which process the reaction is carried out in the presence of an effective amount of a catalytic system comprising at least one copper/butadienylphosphine complex.

17 Claims, No Drawings

(56) References Cited

OTHER PUBLICATIONS

Kang et al., "Copper-catalyzed N-Arylation of Aryl Iodides with Benzamides or Nitrogen Heterocycles in the Presence of Entylenediamine," *Synlett*, No. 3, 2002, pp. 427-430.

Klapars et al., "A General and Efficient Copper Catalyst for the Amidation of Aryl Halides and the N-Arylation of Nitrogen Heterocycles," *J. Am. Chem. Soc,.* vol. 123, 2001, pp. 7727-7729.

International Search Report issued for International Application No. PCT/IB2008/000984 on Nov. 11, 2008.

Teulade et al., "A General One-Pot Synthesis of 1,3-Butadienyl Phosphanes," *Tetrahedron Letters*; 1989; vol. 30, No. 46, pp. 6327-6330.

Taillefer et al., "Reactivity of lithium diphenylphosphonium diylides towards phosphorus electrophiles: Synthesis of $\alpha,\beta$-unsaturated phosphorus compounds," *Journal of Organometallic Chemistry*, 2001, vol. 624, pp. 307-315.

Beletskaya et al., "Copper in cross-coupling reactions the post-Ullmann chemistry," *Coordination Chemistry Reviews*, 2004, vol. 248, pp. 2337-2364.

Hennessy et al., "A General and Mild Copper-Catalyzed Arylation of Diethyl Malonate," *Organic Letters*, vol. 4, No. 2, pp. 269-272 (2002).

\* cited by examiner

METHOD FOR THE PREPARATION OF PHOSPHINE BUTADIENE LIGANDS, COMPLEXES THEREOF WITH COPPER AND USE THEREOF IN CATALYSIS

This application is a divisional of U.S. application Ser. No. 12/450,940 filed Oct. 19, 2009, which is a U.S. national stage application of PCT/IB2008/000984 filed Apr. 21, 2008, which claims priority to FR 07 02878 filed Apr. 20, 2007. Each of these prior applications is incorporated herein by reference in its entirety.

The present invention relates to a process for the preparation of phosphorus-comprising ligands of butadienylphosphine type and to their applications, in particular as ligands for catalytic metals used in reactions for the formation of carbon-carbon and carbon-heteroatom bonds.

Butadienyl phosphorus-comprising derivatives have been known since the 1960s and are of interest in organic synthesis as a result of their electrophilic nature and their biological activity, in particular antiviral activity.

With the development of asymmetric synthesis, butadienyl phosphorus-comprising derivatives today form the subject of intensive research for their great importance in coordination chemistry by the presence, in these derivatives, of two ligands much employed in coordination chemistry: the phosphine ligand and the butadiene ligand.

Processes for the synthesis of derivatives of butadienylphosphine type are currently few in number. They generally employ sophisticated starting compounds and/or numerous synthetic stages, thus resulting in mediocre overall yields.

Thus, for example, M. D. Fryzuk et al. (*J. Org. Chem.*, (1988), 53, 4425-4426) disclose a process for the preparation of butadienylphosphines in two stages, the first stage consisting of a hydrozirconation of a conjugated enyne, thus rendering the process relatively complex to carry out.

Z. Xi et al. (*Tetrahedron Lett.*, (2004), 45, 2427-2429) also bring in an alkyne as starting compound, which alkyne is reacted with a zirconium complex.

M. P. Teulade and P. Savignac (*Tetrahedron Lett.*, (1989), 30(46), 6327-6330) provide a general synthesis of butadienylphosphines based on a Wittig-Horner reaction starting from cyclic phosphonates, and J. L. Cabioch and J. M. Denis (*J. Organomet. Chem.*, (1989), 377(2-3), 227-233) provide, for their part, an example of the synthesis of an unsubstituted primary butadienylphosphine starting from the corresponding phosphonate in the presence of an aluminum salt.

Yet other syntheses have been described; however, all comprise a large number of stages, require starting materials which are expensive or difficult to employ or to prepare, result in the desired products only with low yields or else do not make possible access to a great variety of butadienylphosphines.

Consequently, a first objective of the present invention consists in providing a synthetic route suited to the preparation of varied butadienylphosphines, with acceptable yields, which is easy to use, advantageously with a minimum of stages, starting from starting compounds which are relatively common or easy to prepare.

It has now been discovered that this first objective, and also others which will become apparent during the description of the invention which follows, is achieved in all or at least in part by virtue of the process for the preparation of butadienylphosphines set out below.

A subject matter of the present invention is first of all the process for the preparation of a butadienylphosphine of formula (1):

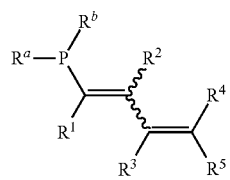

(1)

in which formula:

$R^a$ and $R^b$, which are identical or different, preferably identical, each represent a radical chosen independently from alkyl, aryl, heteroaryl, monoalkylamino, dialkylamino, alkoxy, aryloxy and heteroaryloxy;

$R^1$, $R^2$, $R^3$, $R^4$ and $R^5$, which are identical or different, are chosen independently from hydrogen, a hydrocarbon radical, an aryl radical and a heteroaryl radical;

said process comprising the stages of:

a) bringing a phosphonium halide of formula (2) into contact with a strong base, in a polar aprotic solvent, for example tetrahydrofuran, at low temperature, generally between −70° C. and 0° C., for example −50° C., to result in the phosphonium diylide (3):

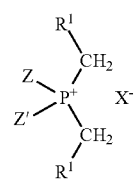

(2)

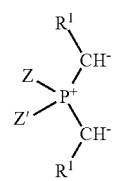

(3)

where $R^1$ is as defined above, Z and Z' have definitions identical to those of $R^a$ and $R^b$ defined above and X represents a halogen atom chosen from fluorine, chlorine, bromine and iodine;

b) which diylide (3) is reacted, in a polar aprotic solvent medium, for example tetrahydrofuran, at a temperature generally of between −70° C. and +10° C., for example −10° C., with a halophosphine (4):

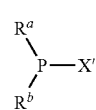

(4)

where $R^a$ and $R^b$ are as defined above and X' represents a halogen atom chosen from fluorine, chlorine, bromine and iodine;

to result in the phosphonium ylide (5a), which undergoes a prototropic rearrangement to give the phosphonium ylide (5b):

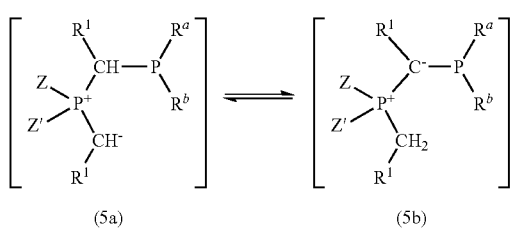

where $R^a$, $R^b$, $R^1$, Z and Z' are as defined above;

c) the ylide (5b) then being brought together, generally at a temperature of between 0° C. and 50° C., for example at ambient temperature, in a polar aprotic solvent, such as tetrahydrofuran, with an α,β-unsaturated carbonyl derivative of formula (6):

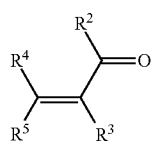

in which $R^2$, $R^3$, $R^4$ and $R^5$ are as defined above,
to result, after removal of the solvent and optional purification, in the butadienylphosphine (1).

In one embodiment, $R^4$ and/or $R^5$ can be connected so as to form, with the carbon atom which carries them, a carbocyclic or heterocyclic group having from 3 to 20 carbon atoms which is saturated, unsaturated, monocyclic or polycyclic, in the latter case comprising two or three rings, it being possible for the adjacent rings to be aromatic in nature.

The process described above can advantageously be carried out in just one reactor (one pot), that is to say without it being necessary to isolate all or some of the intermediates. However, of course and if desired, it is possible to isolate one or more of the intermediates, advantageously when they are stable.

The strong base used for the preparation of the phosphonium diylide (3) described above is generally a metal base, that is to say a strong base comprising one or more metals advantageously chosen from alkali metals and alkaline earth metals, in particular from lithium, sodium, potassium, magnesium, calcium and barium. Strong lithium bases are preferred, in particular butyllithium. In this case, the counterion of the phosphonium diylide (3) is the lithium cation.

In the present invention, the following terms have the meanings below, unless otherwise indicated:
  "alkyl" represents a saturated linear or branched hydrocarbon radical comprising from 1 to 10 carbon atoms, preferably from 1 to 6 carbon atoms, in particular the methyl radical, the ethyl radical, the propyl radicals, the butyl radicals, the pentyl radicals, the hexyl radicals, the heptyl radicals, the octyl radicals, the nonyl radicals and the decyl radicals;
  "aryl" represents a mono- or polycyclic aromatic hydrocarbon radical, for example the phenyl radical and the naphthyl radical;
  "heteroaryl" represents a mono- or polycyclic aromatic hydrocarbon radical additionally comprising one or more identical or different heteroatoms chosen from nitrogen, oxygen or sulfur, each of the rings comprising 5 or 6 members; examples of heteroaryl radicals are the pyridyl radicals, the quinolyl radicals, the imidazolyl radicals and the tetrazolyl radicals, without this list constituting any limitation;
  "hydrocarbon radical" as indicated for the $R^1$, $R^2$, $R^3$, $R^4$ and $R^5$ radicals represents a linear, branched or cyclic (mono- or polycyclic) hydrocarbon radical comprising from 1 to 20 carbon atoms and being able to comprise one or more unsaturations in the form of double and/or triple bond(s), for example, and without implied limitation, methyl, ethyl, propyl, isopropyl, butyl, isobutyl, sec-butyl, tert-butyl, cyclohexyl, benzyl, phenyl, vinyl, allyl and others;
  in the terms "alkoxy", "aryloxy", "heteroaryloxy", "monoalkylamino" and "dialkylamino", the definitions of the terms alkyl-, aryl- and heteroaryl- correspond to the generic terms defined above.

All the radicals having the definitions appearing above can optionally be substituted by one or more halogen atoms, advantageously chosen from fluorine, chlorine, bromine and iodine, by one or more linear or branched alkyl, alkenyl and/or alkynyl radicals comprising from 1 to 10 carbon atoms, or by one or more hydroxyl, alkoxy, alkenyloxy, alkynyloxy, aryl, heteroaryl, amino, alkylamino, dialkylamino, carboxy, carbonyl, carbonylamino, carbonylalkylamino, carbonyldialkylamino radicals, it being possible for the substituents to be identical or different.

In the expanded formula of the compound of formula (1) shown above, the bonds in "wavy" lines indicate that the two double bonds can occur in the cis or trans configuration, that is to say that the butadienylphosphine of formula (1) can be of E or Z configuration.

The butadienylphosphines obtained according to the process of the invention can be specifically of Z configuration (formula (1Z)) or of E configuration (formula (1E)) or in the form of a mixture in all proportions:

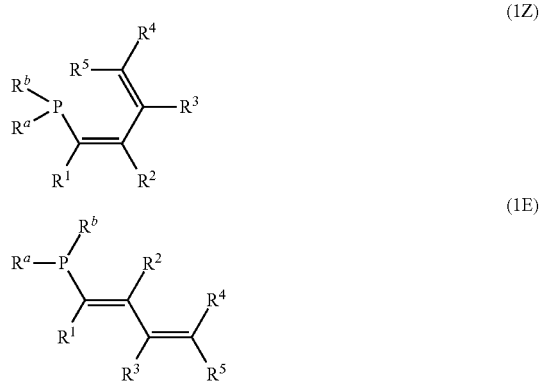

The E and Z isomers of the phosphines obtained according to the process of the present invention can be separated, if necessary, according to conventional methods or processes known to a person skilled in the art.

Depending on the applications envisaged, preference is given to the butadienylphosphines of Z configuration or to the butadienylphosphines of E configuration or else to the mixtures of the E and Z butadienylphosphines in all proportions.

The process of the invention is particularly well suited to the preparation of the butadienylphosphines of formula (1), of Z or E configuration, in which:
  $R^a$ and $R^b$, which are identical or different, each represent a radical chosen independently from alkyl, in particular methyl, ethyl, propyl or butyl; aryl, in particular phenyl or naphthyl; heteroaryl, in particular pyridyl or quinolyl; and, preferably, $R^a$ and $R^b$ are identical and each represent phenyl;

$R^1$ represents hydrogen or alkyl, in particular methyl, ethyl or propyl; preferably, $R^1$ represents hydrogen;

$R^2$, $R^3$ and $R^4$, which are identical or different, are chosen independently from hydrogen, an alkyl radical, an aryl radical and a heteroaryl radical, in particular from hydrogen and an alkyl radical, especially methyl, ethyl or propyl;

$R^5$ is chosen from hydrogen, an alkyl radical, an aryl radical and a heteroaryl radical; preferably, $R^5$ represents alkyl, in particular methyl, ethyl, propyl, butyl or pentyl, or also represents phenyl, naphthyl, pyridyl or quinolyl.

The process of the invention makes it possible in particular to obtain the butadienylphosphines (Z)-Ph($C_4H_4$)PPh$_2$, (E)-Ph ($C_4H_4$)PPh$_2$, (Z)—CH$_3$($C_4H_4$)PPh$_2$ and (E)-CH$_3$Ph ($C_4H_4$)PPh$_2$, where Ph represents phenyl.

The process described above makes it possible to obtain the butadienylphosphines of formula (1) from compounds which are readily available commercially or are easily prepared from procedures known from the literature. In addition, the low number of stages of the process makes it easy to operate.

As indicated above, the process can advantageously be carried out in just one operation (one pot), that is to say without it being necessary to isolate and/or to purify the synthetic intermediates. However, it is possible to isolate and/or purify the intermediates, for example for the purpose of studying the satisfactory progression of the reaction or its kinetics, of analyzing the intermediates formed, and others.

The butadienylphosphines of formula (1), the process of preparation of which represents a first subject matter of the present invention, can entirely advantageously be used as ligands for copper in order to form complexes.

This is because butadienylphosphines are of great interest in coordination chemistry and in catalysis due to the fact that they combine two ligands of great importance in organometallic chemistry: conjugated dienes and phosphines.

Such complexes of copper with at least one butadienylphosphine of formula (1) as defined supra constitute another subject matter of the present invention.

The complexes according to the invention can be represented schematically under the form Pho-Bu/Cu, where Pho-Bu represents a butadienylphosphine of formula (1) defined above and Cu represents a copper atom. This schematic representation does not in any way indicate the number of moles of butadienylphosphine present, with respect to the number of copper atoms present.

The term "monomer complex" is used to describe a Pho-Bu/Cu complex which comprises one copper atom, the term "dimer complex" is used to describe a Pho-Bu/Cu complex which comprises two copper atoms, the term "trimer complex" is used to describe a Pho-Bu/Cu complex which comprises three copper atoms, and the like.

The invention also relates to phenyl- or methylbutadienyl-diphenylphosphine/copper iodide monomer complexes [Ph-CH=CH—CH=CH—PPh$_2$]$_2$CuI (iododi{η-[(4-phenyl-1,3-butadienyl)diphenylphosphine]}copper complex) and [CH$_3$—CH=CH—CH=CH—PPh$_2$]$_2$CuI (iododi{η-[(4-methyl-1,3-butadienyl)diphenylphosphine]}copper complex), where Ph represents the phenyl radical.

The Pho-Bu/Cu complexes defined above can be prepared according to conventional techniques known to a person skilled in the art. For example, the Pho-Bu/Cu complexes can be prepared by bringing at least one butadienylphosphine, in particular of formula (1) defined supra, into contact with metallic copper or a copper (copper(I) or copper(II)) derivative, for example a copper halide, such as cupric or cuprous iodide, bromide or chloride, or other derivatives, in particular organocopper compounds, for example copper acetylacetonate.

The reaction is generally carried out under an inert atmosphere, for example under nitrogen or argon, in an organic solvent medium, preferably a polar aprotic solvent, for example acetonitrile. The complexing reaction is usually carried out at a temperature of between 0° C. and 80° C., depending on the nature of the compounds present, and the reaction temperature is generally ambient temperature.

The complex is generally obtained in the form of a precipitate which is isolated from the reaction medium according to techniques known per se, for example by filtration, and optionally recrystallization from a solvent, advantageously identical to that used for the complexing reaction.

According to an alternative form, the Pho-Bu/Cu complex can advantageously be prepared in situ in the reaction medium for the reaction catalyzed by the Pho-Bu/Cu complex. Such an alternative form is illustrated in the arylation examples (examples C) which follow.

Because of their very great advantage in catalysis, copper/butadienylphosphine complexes, in particular those of Z configuration, are applied entirely appropriately as catalytic system for reactions for the creation of carbon-carbon (C—C) or carbon-heteroatom (C-HE) bonds according to the "Ullmann process" (F. Ullmann and H. Kipper, *Ber. Dtsch. Chem. Ges.*, 1095, 38, 2120-2126).

The copper-catalyzed Ullmann reaction is one of the most widely used methods industrially due to the attractive cost of copper, in comparison with the costs of other noble metals, such as palladium, ruthenium and others.

Recently, Buchwald et al. (*J. Am. Chem. Soc.*, 2001, 123, 7727-7729) have provided for the use of conventional copper ligands in carrying out this copper-catalyzed reaction. International patent application WO-A-03/101966 describes copper ligands which make possible a reaction of Ullmann type under mild conditions, with catalytic amounts of copper. These ligands are mainly ligands of oxime type which require a specific synthesis and consequently result in relatively expensive reaction products.

Thus, another objective of the invention is to provide copper ligands which are easier to prepare and which result in lower reaction costs than those generated to date for coupling reactions of Ullmann type. As other objective, the present invention is targeted at obtaining synthetic yields which are further improved, in comparison with the yields obtained with the processes known in the field.

According to another aspect, the present invention relates to a process for the creation of a carbon-carbon (C—C) bond or of a carbon-heteroatom (C-HE) bond by reacting a compound carrying a leaving group with a nucleophilic compound carrying a carbon atom or a heteroatom (HE) capable of replacing the leaving group, thus creating a C—C or C-HE bond, in which process the reaction is carried out in the presence of an effective amount of a catalytic system comprising at least one copper/butadienylphosphine complex.

The inventors have now discovered that catalytic systems based on copper complexed with a butadienylphosphine make it possible to bring about the creation of a carbon-carbon (C—C) bond or of a carbon-heteroatom (C-HE) bond by reacting a compound carrying a leaving group with a nucleophilic compound carrying a carbon atom or a heteroatom (HE) capable of replacing the leaving group, thus creating a C—C or C-HE bond.

The general scheme of the process according to the present invention can be illustrated as follows:

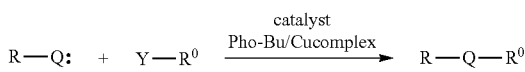

in which:
Y—R⁰ represents a compound carrying a leaving group Y; and
R-Q: represents a nucleophilic compound, R being the residue of said nucleophilic compound and Q being a carbon atom or a heteroatom (HE) which can replace said leaving group Y.

According to a first alternative form of the process of the present invention, an arylation reaction is carried out by reacting an aromatic compound carrying a leaving group with a nucleophilic compound.

According to another alternative form of the process of the invention, a vinylation or alkynylation reaction is carried out by respectively reacting, with a nucleophilic compound, a compound comprising a double bond or a triple bond in the α position with respect to a leaving group.

In the account which follows of the present invention, the term "arylation" is used in its broad sense, since the use is envisaged of an unsaturated compound carrying a leaving group which is either of unsaturated aliphatic type or of carbocyclic or heterocyclic aromatic type.

"Nucleophilic compound" is understood to mean a hydrocarbon organic compound, both acyclic and cyclic or polycyclic, the characteristic of which is to comprise at least one atom carrying a free doublet, which may or may not comprise a charge, and preferably a nitrogen, oxygen, sulfur, boron or phosphorus atom, or to comprise a carbon atom which can donate its electron pair.

As mentioned above, the nucleophilic compound comprises at least one atom carrying a free doublet which can be contributed by a functional group and/or a carbanion.

Mention may in particular be made, as functional groups and/or carbanions comprising said at least one atom, of the following atoms and groups:

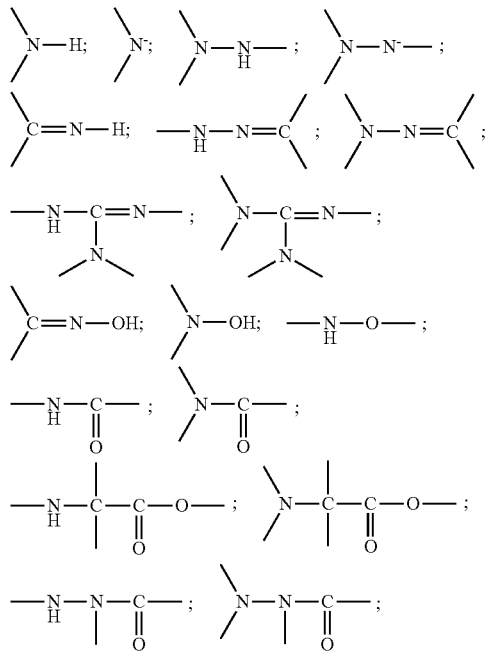

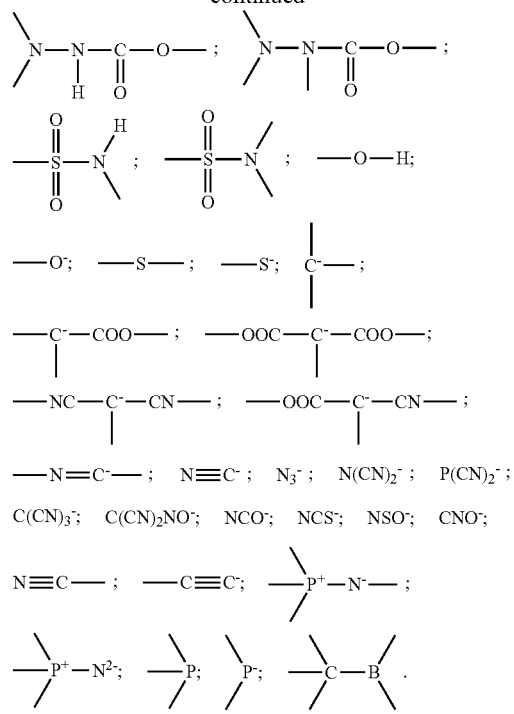

According to another alternative form of the invention, the nucleophilic compound comprises at least one nitrogen atom carrying a free doublet included in a saturated, unsaturated or aromatic ring; the ring generally comprises from 3 to 8 atoms.

It should be noted that, when the nucleophilic compound comprises a functional group, examples of which are given above, which carries one or more negative charges, said compound then occurs in a salified form. The counterion is generally a metal cation, such as an alkali metal, preferably lithium, sodium or potassium, or an alkaline earth metal, preferably calcium, or the residue of an organometallic compound, such as, in particular, an organomagnesium or organozinc compound.

A first advantage of the process of the invention is to carry out the reaction at moderate temperature.

Another advantage is to be able to use a broad range of agents for the coupling, in particular of agents for the arylation, of nucleophiles, not only iodides but also bromides, chlorides or triflates, in particular aryl iodides, aryl bromides, aryl chlorides or aryl triflates.

Another advantage of the process of the invention is to resort to catalysis via copper rather than palladium or nickel, that is to say a catalyst which is less toxic and which is additionally advantageous from the economic viewpoint.

The process of the invention concerns a large number of nucleophilic compounds and examples are given below, by way of illustration, without any limiting nature.

A first category of substrates (nucleophilic compounds) to which the process of the invention applies comprises nitrogenous organic derivatives and more particularly primary or secondary amines; hydrazine or hydrazone derivatives; amides; sulfonamides; urea derivatives; or heterocyclic derivatives, preferably nitrogen-comprising and/or sulfur-comprising heterocyclic derivatives.

More specifically, the primary or secondary amines can be represented by the general formula (Ia):

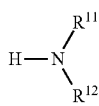

(Ia)

in which formula (Ia):
$R^{11}$ and $R^{12}$, which are identical or different, are chosen from hydrogen, a hydrocarbon radical (1 to 20 carbon atoms, as defined above), an aryl radical or a heteroaryl radical and from any sequence of two or more of the abovementioned groups, it being understood that at most one of the $R^{11}$ and $R^{12}$ groups represents a hydrogen atom.

The amines preferably employed correspond to the formula (Ia) in which $R^{11}$ and $R^{12}$, which are identical or different, represent a $C_1$ to $C_{15}$, preferably $C_1$ to $C_{10}$, alkyl group, a $C_3$ to $C_8$, preferably $C_5$ or $C_6$, cycloalkyl group, or a $C_6$ to $C_{12}$ aryl or arylalkyl group.

Mention may be made, as more particular examples of $R^{11}$ and $R^{12}$ groups, of $C_1$ to $C_4$ alkyl, phenyl, naphthyl or benzyl groups.

Mention may be made, as more specific examples of amines of formula (Ia), of aniline, N-methylaniline, diphenylamine, benzylamine and dibenzylamine.

The present invention does not exclude the presence of one or more unsaturations in the hydrocarbon chain(s), such as one or more double and/or triple bonds, which may be conjugated or nonconjugated.

The hydrocarbon chain(s) can also be interrupted by one or more heteroatoms (for example, oxygen, sulfur, nitrogen or phosphorus) and/or by a nonreactive functional group, such as, for example, —CO—.

It should be noted that the amino group can be in the form of anions. The counterion is then a metal cation, preferably an alkali metal cation and more preferably sodium or potassium. Mention may be made, as examples of such compounds, of sodium amide or potassium amide.

The hydrocarbon chain can optionally carry one or more substituents, as indicated above, in particular atoms, groups or radicals chosen from halogen, ester, amino, alkylphosphine and/or arylphosphine, insofar as they do not interfere.

The saturated or unsaturated, linear or branched acyclic aliphatic groups can optionally carry a cyclic substituent. The term "ring" denotes a saturated, unsaturated or aromatic carbocylic or heterocyclic ring.

The acyclic aliphatic group can be connected to the ring via a valence bond, a heteroatom or a functional group, such as oxy, carbonyl, carboxyl, sulfonyl, and the like.

It is possible to envisage, as examples of cyclic substituents, cycloaliphatic, aromatic or heterocyclic substituents, in particular cycloaliphatic substituents comprising 6 carbon atoms in the ring or benzene substituents, these cyclic substituents themselves optionally carrying any substituent, insofar as they do not interfere with the reactions occurring in the process of the invention. Mention may in particular be made of the alkyl or alkoxy groups comprising from 1 to 4 carbon atoms.

Among the aliphatic groups carrying a cyclic substituent, cycloalkylalkyl groups, for example cyclohexylalkyl groups, or arylalkyl groups, preferably $C_7$ to $C_{12}$ arylalkyl groups, in particular benzyl or phenylethyl groups, are more particularly targeted.

In the general formula (Ia), the $R^{11}$ and $R^{12}$ groups can also represent, independently of one another, a saturated carbocyclic group or a carbocyclic group comprising one or two unsaturations in the ring, generally a $C_3$ to $C_8$ ring, preferably comprising 6 carbon atoms in the ring; it being possible for said ring to be substituted. Mention may be made, as preferred examples of groups of this type, of cyclohexyl groups which are optionally substituted, in particular by linear or branched alkyl groups having from 1 to 4 carbon atoms.

The $R^{11}$ and $R^{12}$ groups can represent, independently of one another, an aromatic hydrocarbon group and in particular a benzene hydrocarbon group corresponding to the general formula ($F_1$):

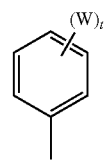

($F_1$)

in which:
t represents 0, 1, 2, 3, 4 or 5; and
W represents a group chosen from linear or branched $C_1$-$C_6$ alkyl, linear or branched $C_1$-$C_6$ alkoxy, linear or branched $C_1$-$C_6$ alkylthio, —$NO_2$, —CN, halogen and $CF_3$.

The aromatic hydrocarbon group can thus be substituted. W illustrates some types of preferred substituents but the list is not limiting.

$R^{11}$ and $R^{12}$ can also represent, independently of one another, a polycyclic aromatic hydrocarbon group with the rings being able to form, with one another, ortho-fused or ortho- and peri-fused systems. Mention may more particularly be made of a naphthyl group, it being possible for said ring to be substituted.

$R^{11}$ and $R^{12}$ can also represent, independently of one another, a polycyclic hydrocarbon group composed of at least two saturated and/or unsaturated carbocycles or of at least two carbocycles, only one of which is aromatic, which form, with one another, ortho- or ortho- and peri-fused systems. Generally, the rings are $C_3$ to $C_8$ rings, preferably $C_6$ rings. Mention may be made, as more specific examples, of the bornyl group or the tetrahydronaphthyl group.

$R^{11}$ and $R^{12}$ can also represent, independently of one another, a saturated, unsaturated or aromatic heterocyclic group comprising in particular 5 or 6 atoms in the ring, including one or two heteroatoms, such as nitrogen atoms (unsubstituted by a hydrogen atom), sulfur atoms and oxygen atoms; it being possible for the carbon atoms of this heterocycle also to be substituted.

$R^{11}$ and $R^{12}$ can also represent a polycyclic heterocyclic group defined as being either a group composed of at least two aromatic or nonaromatic heterocycles comprising at least one heteroatom in each ring and forming, with one another, ortho- or ortho- and peri-fused systems or a group composed of at least one aromatic or nonaromatic hydrocarbon ring and at least one aromatic or nonaromatic heterocycle forming, with one another, ortho- or ortho- and peri-fused systems, it being possible for the carbon atoms of said rings optionally to be substituted.

Mention may be made, as examples of $R^{11}$ and $R^{12}$ groups of heterocyclic type, inter alia, of the furyl, thienyl, isoxazolyl, furazanyl, isothiazolyl, pyridyl, pyridazinyl, pyrimidinyl, pyranyl or phosphino groups and the quinolyl, naphthyridinyl, benzopyranyl or benzofuranyl groups.

The number of substituents present in each ring depends on the carbon fusion of the ring and on the presence or absence of unsaturation in the ring. The maximum number of substituents capable of being carried by a ring is easily determined by a person skilled in the art.

Other nucleophilic compounds capable of being employed in the process of the invention are, for example, the hydrazine derivatives corresponding to the formula (Ib):

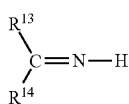

(Ib)

in which:

$R^{13}$ and $R^{14}$, which are identical or different, have the meanings given for $R^{11}$ and $R^{12}$ in the formula (Ia) and at most one of the $R^3$ and $R^4$ groups represents a hydrogen atom.

The $R^{13}$ and $R^{14}$ groups more particularly represent a $C_1$ to $C_{15}$, preferably $C_1$ to $C_{10}$, alkyl group, a $C_3$ to $C_8$, preferably $C_5$ or $C_6$, cycloalkyl group, or a $C_6$ to $C_{12}$ aryl or arylalkyl group. More preferably, $R^{13}$ and $R^{14}$ represent a $C_1$ to $C_4$ alkyl, phenyl, benzyl or naphthyl group.

Mention may be made, as other nucleophiles, of oximes and hydroxylamines, which can be represented by the general formulae (Ic) and (Id) respectively:

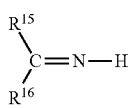

(Ic)

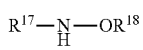

(Id)

in which formulae:

$R^{15}$ and $R^{16}$, which are identical or different, have the definitions given for $R^{11}$ and $R^{12}$ in the formula (Ia) and at most one of the $R^{15}$ and $R^{16}$ groups represents a hydrogen atom;

$R^{17}$ has the definitions given for $R^{11}$ or $R^{12}$ in the formula (Ia), with the exception of the hydrogen atom; and $R^{18}$ is chosen from the hydrogen atom, a saturated or unsaturated, linear or branched acyclic aliphatic group and a saturated or unsaturated monocyclic or polycyclic carbocyclic group, and from any sequence of two or more of said groups.

Preferred examples of oximes or hydroxylamines of formulae (Ic) and (Id) respectively are those for which $R^{15}$, $R^{16}$ and $R^{17}$ represent $C_1$ to $C_{15}$, preferably $C_1$ to $C_{10}$, alkyl, $C_3$ to $C_8$, preferably $C_5$ or $C_6$, cycloalkyl or $C_6$ to $C_{12}$ aryl or arylalkyl.

Mention may be made, as more particular examples of $R^{15}$, $R^{16}$ and $R^{17}$ groups, of $C_1$ to $C_4$ alkyl, phenyl, naphthyl or benzyl groups. With regard to $R^{18}$, it preferably represents $C_1$ to $C_4$ alkyl or benzyl.

According to another aspect, the present invention employs nucleophilic compounds of hydrazine type which can be represented by the following formula (Ie):

(Ie)

in which:

$R^{19}$, $R^{20}$ and $R^{21}$, which are identical or different, have the definitions given for $R^{11}$ and $R^{12}$ in the formula (Ia);

$R^{21}$ represents a hydrogen atom or a protective group G; and at least one of the $R^{19}$, $R^{20}$ and $R^{21}$ groups does not represent a hydrogen atom;

or else $R^{19}$ and $R^{20}$ can together form, with the nitrogen atom which carries them, a saturated, unsaturated or aromatic monocyclic or polycyclic $C_3$-$C_{20}$ heterocyclic group.

Preferred hydrazines of formula (Ie) above are those in which $R^{19}$ and $R^{20}$, which are identical or different, represent $C_1$-$C_{15}$, preferably $C_1$-$C_{10}$ alkyl, $C_3$-$C_8$, preferably $C_5$ or $C_6$, cycloalkyl or $C_6$-$C_{12}$ aryl or arylalkyl. More preferably, the hydrazines are those of formula (Ie) in which $R^{19}$ and $R^{20}$, which are identical or different, represent $C_1$ to $C_4$ alkyl, phenyl, benzyl or naphthyl.

$R^{19}$ and $R^{20}$ can be connected together, so as to form, with the nitrogen atom which carries them, a saturated, unsaturated or aromatic monocyclic or polycyclic $C_3$-$C_{20}$ heterocyclic group comprising two or three ortho-fused rings, that is to say at least two rings which have two carbon atoms in common.

For the polycyclic compounds, the number of atoms of each ring can preferably vary between 3 and 6. According to a preferred embodiment, $R^{19}$ and $R^{20}$ together form a cyclohexane or fluorenone ring.

In the above formula (Ie), $R^{21}$ preferably represents a hydrogen atom, alkyl (preferably $C_1$-$C_{12}$), alkenyl or alkynyl (preferably $C_2$-$C_{12}$), cycloalkyl (preferably $C_3$-$C_{12}$), or aryl or arylalkyl (preferably $C_6$-$C_{12}$). More preferably, $R^{21}$ represents a hydrogen atom or a $C_1$-$C_4$ alkyl group.

It should be noted that, when the nucleophilic compound comprises an $NH_2$ group, both hydrogen atoms can react. In such a case, and in order to increase the selectivity of the reaction, one or both hydrogen atoms can advantageously be masked by the use of a protective group. Such protective groups are well known in the field and mention may be made of the protective groups commonly used, such as, for example, acyl (acetyl, benzoyl), BOC (butoxycarbonyl), CBZ (carbobenzoxy), FMOC (trifluoromethyloxycarbonyl) or MSOC (2-(methane-sulfenyl)ethoxycarbonyl) groups. Reference may be made, on this subject, for example, to the work by T. W. Greene et al., *Protective Groups in Organic Synthesis*, 2$^{nd}$ edition, John Wiley & Sons Inc., as regards the reactions for protecting and deprotecting amino groups.

Other nucleophilic compounds which can be employed in the process of the present invention are the compounds of hydrazone type, which can be represented by the formula (If):

(If)

in which:

$R^{22}$, $R^{23}$ and $R^{24}$, which are identical or different, have the definitions given for $R^{11}$ and $R^{12}$ in the formula (Ia);

at most one of the $R^{22}$ and $R^{23}$ groups represents the hydrogen atom;

or else $R^{22}$ and $R^{23}$ can together form, with the nitrogen atom which carries them, a saturated, unsaturated or aromatic monocyclic or polycyclic $C_3$-$C_{20}$ carbocyclic or heterocyclic group.

Preferred examples of hydrazones of above formula (If) are those in which $R^{22}$ and $R^{23}$, which are identical or different, represent $C_1$-$C_{15}$, preferably $C_1$-$C_{18}$, alkyl, $C_3$-$C_8$, preferably $C_5$ or $C_6$, cycloalkyl, or $C_6$-$C_{12}$ aryl or arylalkyl. More preferably, examples of hydrazones of formula (If) are those in which $R^{22}$ and $R^{23}$, which are identical or different, represent $C_1$ to $C_4$ alkyl, phenyl, benzyl or naphthyl.

$R^{22}$ and $R^{23}$ can together form, with the nitrogen atom which carries them, a saturated, unsaturated or aromatic monocyclic or polycyclic $C_3$-$C_{20}$ carbocyclic or heterocyclic group comprising two or three ortho-fused rings.

For the polycyclic compounds, the number of atoms of each ring can preferably vary between 3 and 6. According to a preferred embodiment, $R^{22}$ and $R^{23}$ together form a cyclohexane or fluorenone ring.

In the above formula (If), $R^{24}$ preferably represents a hydrogen atom or an alkyl (preferably $C_1$-$C_{12}$), alkenyl or alkynyl (preferably $C_2$-$C_{12}$), cycloalkyl (preferably $C_3$-$C_{12}$), or aryl or arylalkyl (preferably $C_6$-$C_{12}$) group. More preferably, $R^{24}$ represents a hydrogen atom or a $C_1$-$C_4$ alkyl group.

The invention is also targeted at the compounds of amide type corresponding more particularly to the formula (Ig):

in which $R^{25}$ and $R^{26}$ have the meanings given for $R^{11}$ and $R^{12}$ in the formula (Ia).

Mention may be made, as examples of compounds of formula (Ig), of oxazolidin-2-one, benzamide and acetamide.

The invention also applies to compounds of sulfonamide type which can, for example, correspond to the formula (Ih):

in which $R^{27}$ and $R^{28}$ have the meanings given for $R^{11}$ and $R^{12}$ in the formula (Ia).

Mention may be made, as example of compounds of formula (Ih), of tosylhydrazide.

Mention may be made, as other types of nucleophilic substrates, of urea derivatives, such as guanidines, which can be represented by the formula (Ii):

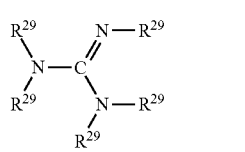

in said formula (Ii), the $R^{29}$ groups, which are identical or different, have the meanings given for $R^{11}$ and $R^{12}$ in the formula (Ia).

Mention may be made, as example of compounds of formula (Ii), of N,N,N',N'-tetramethylguanidine.

Yet other examples of nucleophilic compounds which can be used in the process of the present invention comprise amino acids and their derivatives, for example those corresponding to the following formula (Ij):

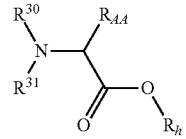

in which:
$R_{AA}$ represents a hydrogen atom or the residue of an amino acid, preferably a hydrogen atom; a linear or branched $C_1$-$C_{12}$ alkyl optionally carrying a functional group; a $C_6$-$C_{12}$ aryl or arylalkyl; or a functional group, preferably a hydroxyl group;
$R^{30}$ and $R^{31}$ have the definitions given for $R^{11}$ and $R^{12}$ in the formula (Ia);
$R_h$ represents a hydrogen atom, a metal cation, preferably an alkali metal cation, or a $C_1$-$C_{12}$ hydrocarbon group, preferably a $C_1$-$C_{12}$ alkyl group.

According to a preferred embodiment, $R_{AA}$ in the above formula (Ij) represents alkyl, optionally comprising a functional group, for example —OH, —NH$_2$, —CO—NH$_2$, —NH—CNH—, —HN—C(O)—NH$_2$, —COOH, —SH or —S—CH$_3$, or an imidazole, pyrrole or pyrazole group.

Examples of such amino acids comprise glycine, cysteine, aspartic acid, glutamic acid or histidine.

Nucleophilic substrates entirely well suited to the use of the process of the invention are the heterocyclic derivatives comprising at least one nucleophilic atom, such as a nitrogen, sulfur or phosphorus atom.

More specifically, such compounds correspond to the general formula (Ik):

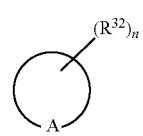

in said formula (Ik):
A symbolizes the residue of a ring forming all or part of an aromatic or nonaromatic, monocyclic or polycyclic heterocyclic system, one of the carbon atoms of which is replaced by at least one nucleophilic atom, such as a nitrogen, sulfur or phosphorus atom;
$R^{32}$, which are identical or different, represent(s) the substituent(s) of the ring;
n represents the number of substituents on the ring.

The invention applies in particular to the monocyclic heterocyclic compounds corresponding to the formula (Ik) in which A symbolizes a saturated, unsaturated or aromatic heterocycle comprising in particular 5 or 6 atoms in the ring which can comprise from 1 to 3 heteroatoms, such as nitrogen, sulfur and oxygen atoms, at least one of which from among them is a nucleophilic atom, such as NH or S.

A can also represent a polycyclic heterocyclic compound defined as being composed of at least two aromatic or nonaromatic heterocycles comprising at least one heteroatom in each ring and forming, with one another, ortho- or ortho- and peri-fused systems or composed of at least one aromatic or nonaromatic carbocycle and at least one aromatic or nonaromatic heterocycle forming, with one another, ortho- or ortho- and peri-fused systems.

It is also possible to start from a substrate resulting from the linking of a saturated, unsaturated or aromatic heterocycle, such as mentioned above, and of a saturated, unsaturated or aromatic carbocycle. Carbocycle is preferably understood to mean a ring of cycloaliphatic or aromatic type having from 3 to 8 carbon atoms, preferably 6 carbon atoms.

It should be noted that the carbon atoms of the heterocycle can optionally be substituted, in their entirety or for a portion of them only, by $R^{32}$ groups.

The number of substituents present on the ring depends on the number of atoms in the ring and on the presence or absence of unsaturations in the ring. The maximum number of substituents capable of being carried by a ring is easily determined by a person skilled in the art.

In the formula (Ik), n is preferably 0, 1, 2, 3 or 4; more preferably, n is equal to 0 or 1.

Examples of substituents are given below but this list does not exhibit a limiting nature.

The $R^{32}$ group or groups, which are identical or different, preferably represent one of the following groups:

a linear or branched $C_1$ to $C_6$, preferably $C_1$ to $C_4$, alkyl group, such as methyl, ethyl, propyl, isopropyl, butyl, isobutyl, sec-butyl or tert-butyl;

a linear or branched $C_2$ to $C_6$, preferably $C_2$ to $C_4$, alkenyl or alkynyl group, such as vinyl or allyl;

a linear or branched $C_1$ to $C_6$, preferably $C_1$ to $C_4$, alkoxy or thioether group, such as the methoxy, ethoxy, propoxy, isopropoxy or butoxy groups, an alkenyloxy group, preferably an allyloxy group, or a phenoxy group;

a cyclohexyl, phenyl or benzyl group;

a group or a functional group, such as hydroxyl, thiol, carboxyl, ester, amide, formyl, acyl, aroyl, amide, urea, isocyanate, thioisocyanate, nitrile, azide, nitro, sulfone, sulfonic, halogen, pseudohalogen or trifluoromethyl.

The present invention applies very particularly to the compounds corresponding to the formula (Ik) in which the $R^{32}$ group or groups more particularly represent an alkyl or alkoxy group.

More particularly, the optionally substituted residue A represents one of the following rings:

a monocyclic heterocycle comprising one or more heteroatoms:

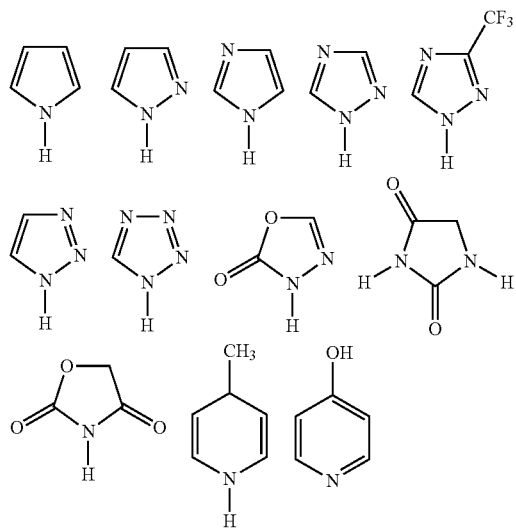

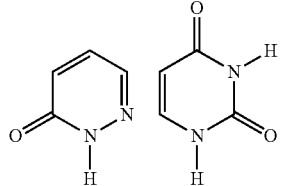

a bicycle comprising a carbocycle and a heterocycle comprising one or more heteroatoms:

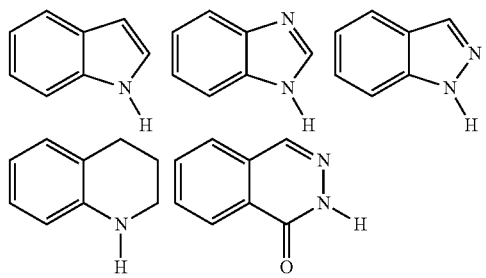

a tricycle comprising at least one carbocycle or one heterocycle comprising one or more heteroatoms:

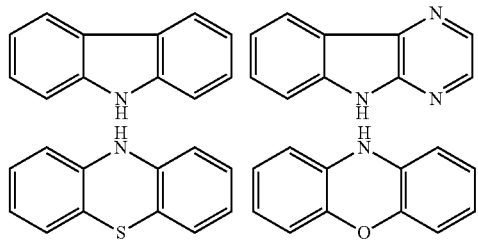

As examples of heterocyclic compounds, it is preferable to use those which correspond to the formula (Ik) in which A represents a ring such as imidazole, pyrazole, triazole, pyrazine, oxadiazole, oxazole, tetrazole, indole, pyrrole, phthalazine, pyridazine or oxazolidine.

As regards the nucleophilic compounds capable of also being employed in the process of the invention, mention may also be made of the compounds of alcohol type or of thiol type which can be represented by the following formula (Im):

in which formula (Im):

$R^{33}$ represents a hydrocarbon group having from 1 to 20 carbon atoms and has the meanings given for $R^{11}$ or $R^{12}$ in the formula (Ia); and Z represents a group of $OM^1$ or $SM^1$ type, in which $M^1$ represents a hydrogen atom or a metal cation, preferably an alkali metal cation.

The preferred compounds correspond to the formula (Im) in which $R^{33}$ represents a hydrocarbon group having from 1 to 20 carbon atoms which can be a saturated or unsaturated, linear or branched acyclic aliphatic group, a saturated, unsaturated or aromatic, monocyclic or polycyclic carbocyclic or heterocyclic group, or any sequence of two or more of the abovementioned groups.

More specifically, $R^{33}$ preferably represents a saturated, linear or branched, acyclic aliphatic group preferably having from 1 to 12 carbon atoms and more preferably from 1 to 4 carbon atoms.

The invention does not exclude the presence of an unsaturation in the hydrocarbon chain, such as one or more double and/or triple bonds, which can be conjugated or nonconjugated.

As mentioned for $R^{11}$ defined in the formula (Ia), the hydrocarbon chain can optionally be interrupted by a heteroatom or a functional group or carry one or more substituents.

In the formula (Im), $R^{33}$ can also represent a saturated or unsaturated carbocyclic group preferably having 5 or 6 carbon atoms in the ring, a saturated or unsaturated heterocyclic group comprising in particular 5 or 6 atoms in the ring, including 1 or 2 heteroatoms, such as nitrogen, sulfur, oxygen or phosphorus atoms, a monocyclic aromatic carbocyclic or heterocyclic group, preferably phenyl, pyridyl, furyl, pyranyl, thiophenyl, thienyl, phospholyl, pyrazolyl, imidazolyl or pyrrolyl, or a fused or nonfused polycyclic aromatic carbocyclic or heterocyclic group, preferably naphtyl.

Provided that $R^{33}$ comprises a ring, the latter can also be substituted. The substituent can have any nature insofar as it does not interfere with the main reaction. The number of substituents is generally at most 4 per ring but is most often equal to 1 or 2. Reference may be made to the definition of $R^{32}$ in the formula (Ik).

The invention is also targeted at the case where $R^{33}$ comprises a sequence of aliphatic and/or cyclic, carbocyclic and/or heterocyclic groups.

An acyclic aliphatic group can be connected to a ring via a valence bond, a heteroatom or a functional group, such as oxy, carbonyl, carboxy, sulfonyl, and the like.

A more particular target is cycloalkylalkyl, for example cyclohexylalkyl, groups or aralkyl groups having from 7 to 12 carbon atoms, in particular benzyl or phenylethyl groups.

The invention is also targeted at a sequence of carbocyclic and/or heterocyclic groups and more particularly a sequence of phenyl groups separated by a valence bond or an atom or functional group, such as oxygen, sulfur, sulfo, sulfonyl, carbonyl, carbonyloxy, imino, carbonylimino, hydrazo, or ($C_1$-$C_{10}$, preferably $C_1$-$C_6$)alkylenediimino.

The saturated or unsaturated, linear or branched acyclic aliphatic group can optionally carry a cyclic substituent. "Ring" is understood to mean a saturated, unsaturated or aromatic carbocyclic or heterocyclic ring.

The preferred compounds of formula (Im) correspond more particularly to the general formula ($Im_1$):

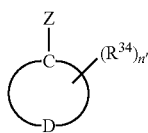

in which:

D symbolizes the residue of a monocyclic or polycyclic aromatic carbocyclic group or a divalent group composed of any sequence of two or more monocyclic aromatic carbocyclic groups;

$R^{34}$ represents one or more identical or different substituents;

Z represents a group of $OM^1$ or $SM^1$ type in which $M^1$ represents a hydrogen atom or a metal cation, preferably an alkali metal cation; and n' represents 0, 1, 2, 3, 4 or 5.

Reference may be made, as examples of $R^{34}$ substituents, to those identified under $R^{32}$ defined in the formula (Ik).

Use is more particularly made, among the compounds of formula ($Im_1$), of those for which the (D) residue represents:

a monocyclic or polycyclic aromatic carbocyclic group with rings which can form, with one another, an ortho-fused system corresponding to the formula ($F_{11}$):

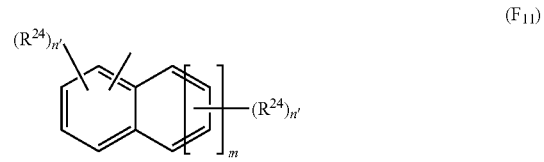

in said formula ($F_{11}$), m represents a number equal to 0, 1 or 2, the $R^{34}$ and n' symbols, which are identical or different, having the meanings given above;

a group composed of a sequence of two or more monocyclic aromatic carbocyclic groups corresponding to the formula ($F_{12}$):

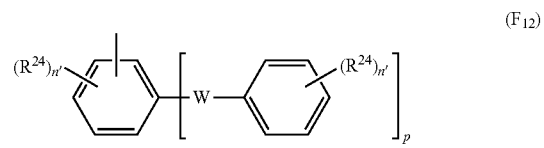

in said formula ($F_{12}$), the $R^{34}$ and n' symbols, which are identical or different, have the meanings given above, p is a number equal to 0, 1, 2 or 3 and W represents a valence bond, a $C_1$ to $C_4$ alkylene or alkylidene group, preferably a methylene or isopropylidene group, or a functional group, such as oxy, carbonyl, carboxy, sulfonyl and others.

The compounds of formula (Im) employed preferably correspond to the formulae ($F_{11}$) and ($F_{12}$), in which:

$R^{34}$ represents a hydrogen atom, a hydroxyl group, a —CHO group, an —$NO_2$ group or a linear or branched alkyl or alkoxy group having from 1 to 6 carbon atoms, preferably from 1 to 4 carbon atoms, more preferably methyl, ethyl, methoxy or ethoxy;

W symbolizes a valence bond, an alkylene or alkylidene group having from 1 to 4 carbon atoms, or an oxygen atom;

m is equal to 0 or 1;

n' is equal to 0, 1 or 2; and p is equal to 0 or 1.

Mention may more particularly be made, by way of illustration of compounds corresponding to the formula (Im), of:

those in which the D residue corresponds to the formula ($F_{11}$) in which m and n' are equal to 0, such as phenol or thiophenol;

those in which the D residue corresponds to the formula ($F_{11}$) in which m is equal to 0 and n' is equal to 1, such as hydroquinone, pyrocatechol, resorcinol, alkylphenols, alkylthiophenols, alkoxyphenols, salicyl aldehyde, para-hydroxybenzaldehyde, methyl salicylate, the methyl ester of para-hydroxybenzoic acid, chlorophenols, nitrophenols or para-acetamidophenol;

those in which the D residue corresponds to the formula ($F_{11}$) in which m is equal to 0 and n' is equal to 2, such as dialkylphenols, vanillin, isovanillin, 2-hydroxy-5-acetamidobenzaldehyde, 2-hydroxy-5-propionamidobenzaldehyde, 4-allyloxybenzaldehyde, dichlorophenols, methylhydroquinone or chlorohydroquinone;

those in which the D residue corresponds to the formula ($F_{11}$) in which m is equal to 0 and n' is equal to 3, such as 4-bromovanillin, 4-hydroxyvanillin, trialkylphenols, 2,4,6-trinitrophenol, 2,6-dichloro-4-nitrophenol, trichlorophenols, dichlorohydroquinones or 3,5-dimethoxy-4-hydroxybenzaldehyde;

those in which the D residue corresponds to the formula ($F_{11}$) in which m is equal to 1 and n' is greater than or equal to 1, such as dihydroxynaphthalene, 4-methoxynaphth-1-ol or 6-bromonaphth-2-ol;

those in which the D residue corresponds to the formula ($F_{12}$) in which p is equal to 1 and n' is greater than or equal to 1, such as 2-phenoxyphenol, 3-phenoxyphenol, phenylhydroquinone, 4,4'-dihydroxybiphenyl, 4,4'-isopropylidenediphenol (bisphenol A), bis(4-hydroxyphenyl)methane, bis (4-hydroxyphenyl) sulfone, bis(4-hydroxyphenyl) sulfoxide or tetrabromobisphenol A.

Mention may be made, among the other nucleophilic compounds belonging to completely different families which are capable of being employed in the process of the invention, of the compounds comprising phosphorus and the compounds comprising phosphorus and nitrogen, preferably those corresponding to the following formulae:

phosphides of formula $(R^{35})_2$—$P^-$ (In);

phosphines of formula $(R^{35})_3$—P (Io);

phosphonium azayldiides of formula $(R^{35})_3$—$P^+$—$N^{2-}$ (Ip);

phosphonium azaylides of formula $(R^{35})_3$—$P^+$—N—$R^{36}$ (Iq);

in which formulae (In) to (Iq), the $R^{35}$ groups, which are identical or different, and the $R^{36}$ group represent:
$C_1$-$C_{12}$ alkyl;
$C_5$-$C_6$ cycloalkyl;
$C_5$-$C_6$ cycloalkyl substituted by one or more $C_1$-$C_4$ alkyl groups or $C_1$-$C_4$ alkoxy groups;
phenylalkyl, the aliphatic part of which has from 1 to 6 carbon atoms;
phenyl; or
phenyl substituted by one or more $C_1$-$C_4$ alkyl groups or $C_1$-$C_4$ alkoxy groups or by one or more halogen atom(s).

Mention may be made, as particularly preferred phosphorus-comprising compounds, of tricyclohexyl-phosphine, trimethylphosphine, triethylphosphine, tri(n-butyl)phosphine, tri(isobutyl)phosphine, tri(tert-butyl)phosphine, tribenzylphosphine, dicyclo-hexylphenylphosphine, triphenylphosphine, dimethyl-phenylphosphine, diethylphenylphosphine or di(tert-butyl)phenylphosphine.

Other compounds capable of being used in the process of the invention are the hydrocarbon derivatives comprising a nucleophilic carbon.

Mention may more particularly be made of the anions of malonate type comprising a —OOC—$HC^-$—COO— group.

Mention may be made of the anions of alkyl malonate type of formula (Ir):

$R^{37}$—OOC—$HC^-$($R^{38}$)—COO—$R^{'37}$ (Ir)

in which:
$R^{37}$ and $R^{'37}$, which are identical or different, represent an alkyl group comprising from 1 to 12 atoms, preferably from 1 to 4 atoms;
$R^{38}$ is chosen from a hydrogen atom; $C_1$-$C_{12}$ alkyl; $C_5$-$C_6$ cycloalkyl; $C_5$-$C_6$ cycloalkyl substituted by one or more $C_1$-$C_4$ alkyls or $C_1$-$C_4$ alkoxys; phenyl; phenyl substituted by one or more $C_1$-$C_4$ alkyls or $C_1$-$C_4$ alkoxys or by one or more halogen atoms; or phenylalkyl, the aliphatic part of which comprises from 1 to 6 carbon atoms.

Mention may also be made of the anions of malononitrile and malonodinitrile type comprising an $R^{37}$—OOC—$HC^-$($R^{38}$)—CN or NC—$HC^-$—CN group respectively, in which $R^{37}$ and $R^{38}$ have the meanings given above.

The compounds of nitrile type comprising an $R^{'28}$—CN group, in which $R^{'28}$ has any nature and has the meanings given for $R^{11}$ in the formula (Ia) and also represents a metal cation, preferably an alkali metal cation, more preferably still lithium, sodium or potassium, are also suitable.

Mention may be made, as examples of nitriles, of acetonitrile, cyanobenzene, optionally carrying one or more substituents on the benzene ring, or ethanal cyanohydrin $CH_3CH(OH)CN$.

Also capable of being employed in the process of the invention are the compounds of acetylenide type, which can be represented schematically by the formula (Is):

$R^{39}$—C≡$C^-$ (Is)

in said formula, $R^{39}$ has any nature and has in particular the meanings given for $R^{11}$ in the formula (Ia) and the counterion is a metal cation, preferably sodium or potassium.

Mention may be made, as more specific examples, of sodium acetylide, potassium acetylide, sodium diacetylide or potassium diacetylide.

Mention may be made, as other categories of nucleophilic compounds which can be employed in the process of the invention, of the compounds of profen type and their derivatives, which can be represented by the following formula (It):

$R^{40}$—$HC^-$—COO—$R^{41}$ (It)

in which formula:
$R^{40}$ has the meanings given for $R^{11}$ in the formula (Ia); and
$R^{41}$ represents an alkyl group having from 1 to 12 carbon atoms, preferably from 1 to 4 atoms.

The preferred compounds are those which correspond to the formula (It) in which $R^{40}$ represents an alkyl group having from 1 to 12 carbon atoms, a cycloalkyl group having 5 or 6 carbon atoms and an aryl group having 6 or 12 carbon atoms, or a nitrogenous heterocycle having 5 or 6 atoms.

Mention may also be made, as nucleophilic compounds, of those comprising a carbanion and for which the counterion is a metal, corresponding to the following formulae:

(Iu₁)

(Iu₂)

(Iu₃)

in which:
the $R^{42}$ group represents:
an alkyl group having from 1 to 12 carbon atoms;
a cycloalkyl group having 5 or 6 carbon atoms;

a cycloalkyl group having 5 or 6 carbon atoms substituted by one or more alkyl radicals having 1 to 4 carbon atoms and/or one or more alkoxy radicals having from 1 to 4 carbon atoms;

a phenylalkyl group, the aliphatic part of which comprises from 1 to 6 carbon atoms;

a phenyl group;

a phenyl group substituted by one or more alkyl radicals having from 1 to 4 carbon atoms or one or more alkoxy radicals having from 1 to 4 carbon atoms or by one or more halogen atoms; or a saturated, unsaturated or aromatic heterocyclic group preferably comprising 5 or 6 atoms and comprising, as heteroatom(s), sulfur, oxygen or nitrogen;

the $R'^{42}$ and $R''^{42}$ groups represent a hydrogen atom or a group such as $R^{42}$;

two of the $R^{42}$, $R'^{42}$ and $R''^{42}$ groups can be connected together to form a saturated, unsaturated or aromatic carbocycle or heterocycle preferably having 5 or 6 carbon atoms;

$M_2$ represents a metal element from Group Ia of the Periodic Table of the Elements;

$M_3$ represents a metal element from Groups IIa and IIb of the Periodic Table of the Elements;

$X_1$ represents a chlorine or bromine atom;

v is the valency of the metal $M_3$; and w is equal to 0 or 1.

In the present text, reference is made, above and in the continuation, to the Periodic Table of the Elements published in the Bulletin de la Société Chimique de France, No. 1 (1966).

Among the compounds of formulae ($Iu_1$) to ($Iu_3$), those which are preferred involve, as metals, lithium, sodium, magnesium or zinc and $X_1$ represents a chlorine atom.

The $R^{42}$, $R'^{42}$ and $R''^{42}$ groups are advantageously a $C_1$-$C_4$ alkyl group, a cyclohexyl group or a phenyl group or said groups can form a benzene, cyclopentadiene, pyridine or thiophene ring.

Mention may be made, as examples, of n-butyllithium, t-butyllithium, phenyllithium, methyl- or ethyl- or phenylmagnesium bromide or chloride, di-phenylmagnesium, dimethyl- or diethylzinc, cyclopenta-dienylzinc, or ethylzinc chloride or bromide.

Recourse may be had, as other nucleophilic compounds capable of being employed, to boronic acids or their derivatives and more particularly to those corresponding to the following formula (Iv):

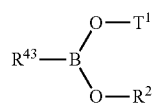

(Iv)

in which:

$R^{43}$ represents a monocyclic or polycyclic aromatic carbocyclic or heterocyclic group; and $T^1$ and $T^2$, which are identical or different, represent a hydrogen atom, a saturated or unsaturated, linear or branched aliphatic group having from 1 to 20 carbon atoms or an $R^{43}$ group.

More specifically, the boronic acid or its derivative corresponds to the formula (Iv) in which the $R^{43}$ group represents an aromatic carbocyclic or heterocyclic group. Thus, $R^{43}$ can take the meanings given above for D in the formula ($Im_1$). However, $R^{43}$ more particularly represents a carbocyclic group, such as a phenyl or naphthyl group, or a heterocyclic group, such as a pyrrolyl, pyridyl, pyrimidinyl, pyridazinyl, pyrazinyl, 1,3-thiazolyl, 1,3,4-thiadiazolyl or thienyl group.

The aromatic ring can also be substituted. The number of substituents is generally at most 4 per ring but is most often equal to 1 or 2. Reference may be made to the definition of $R^{32}$ of the formula (Ik) for examples of substituents.

The preferred substituents are alkyl or alkoxy groups having from 1 to 4 carbon atoms, an amino group, a nitro group, a cyano group, a halogen atom or a trifluoromethyl group.

As regards $T^1$ and $T^2$, which can be identical or different, they more particularly represent a hydrogen atom or a linear or branched acyclic aliphatic group which has from 1 to 20 carbon atoms and which is saturated or comprises one or more unsaturations in the form of double and/or triple bond(s) in the chain, preferably from 1 to 3 unsaturations, which are preferably simple or conjugated double bonds.

$T^1$ and $T^2$ preferably represent an alkyl group having from 1 to 10 carbon atoms, preferably from 1 to 4 carbon atoms, or an alkenyl group having from 2 to 10 carbon atoms, preferably a vinyl or 1-methylvinyl group.

$T^1$ and $T^2$ can additionally take the meanings given for $R^{43}$ and in particular any ring can also carry a substituent as described above.

$R^{43}$ preferably represents a phenyl group.

It will not be departing from the scope of the present invention to resort to boronic acid derivatives, such as anhydrides and esters, more particularly alkyl esters having from 1 to 4 carbon atoms.

Mention may in particular be made, as examples of arylboronic acids, of benzeneboronic acid, 2-thiopheneboronic acid, 3-thiopheneboronic acid, 4-methylbenzeneboronic acid, 3-methylthiophene-2-boronic acid, 3-aminobenzeneboronic acid, 3-aminobenzeneboronic acid hemisulfate, 3-fluorobenzeneboronic acid, 4-fluorobenzeneboronic acid, 2-formylbenzeneboronic acid, 3-formylbenzeneboronic acid, 4-formylbenzeneboronic acid, 2-methoxybenzeneboronic acid, 3-methoxybenzeneboronic acid, 4-methoxybenzeneboronic acid, 4-chlorobenzeneboronic acid, 5-chlorothiophene-2-boronic acid, benzo[b]furan-2-boronic acid, 4-carboxy-benzeneboronic acid, 2,4,6-trimethylbenzeneboronic acid, 3-nitrobenzeneboronic acid, 4-(methyl-thio)benzeneboronic acid, 1-naphthaleneboronic acid, 2-naphthaleneboronic acid, 2-methoxy-1-naphthaleneboronic acid, 3-chloro-4-fluorobenzeneboronic acid, 3-acetamidobenzeneboronic acid, 3-trifluoromethylbenzeneboronic acid, 4-trifluoromethylbenzeneboronic acid, 2,4-dichlorobenzeneboronic acid, 3,5-dichlorobenzeneboronic acid, 3,5-bis (trifluoromethyl)benzeneboronic acid, 4,4'-biphenyldiboronic acid and the esters and anhydrides of these acids.

The present description provides lists of nucleophilic compounds but are not under any circumstances limiting and any type of nucleophilic compound can be envisaged.

As indicated above and according to the process of the present invention, a —C—C— or —C-HE- bond (where HE represents O, S, P, N, Si, B and others) can be created by reaction of a nucleophilic compound, such as those which have just been described above, with a compound carrying a leaving group, in particular a compound comprising an unsaturated bond situated in the a position with respect to a leaving group.

More specifically, the compound carrying a leaving group is represented by the general formula (II):

 (II)

in which formula $R^0$ represents a hydrocarbon group comprising from 2 to 20 carbon atoms and optionally has at least one unsaturation (a double or triple bond) situated in the α position with respect to a leaving group Y or represents a monocyclic or polycyclic aromatic carbocyclic and/or heterocyclic group.

In accordance with the process of the invention, the compound of formula (I) is reacted with a compound of formula (II) in which:

$R^0$ represents an aliphatic hydrocarbon group optionally comprising a double bond and/or a triple bond in the α position with respect to the leaving group or a cyclic hydrocarbon group comprising an unsaturation carrying the leaving group; or $R^0$ represents a monocyclic or polycyclic aromatic carbocyclic and/or heterocyclic group;

Y represents a leaving group, preferably a halogen atom or a sulfonic ester group of formula —OSO$_2$—R$^e$, in which R$^e$ is a hydrocarbon group.

The compound of formula (II) will be subsequently denoted by "compound carrying a leaving group".

In the formula of the sulfonic ester group, R$^e$ is a hydrocarbon group of any nature. However, given that Y is a leaving group, it is advantageous from an economic viewpoint for R$^e$ to be simple in nature and to more particularly represent a linear or branched alkyl group having from 1 to 4 carbon atoms, preferably a methyl or ethyl group; however, it can also represent, for example, a phenyl or tolyl group or a trifluoromethyl group.

Among the Y groups, the preferred group is a triflate group, which corresponds to an R$^e$ group representing a trifluoromethyl group.

The choice is preferably made, as preferred leaving groups, of a bromine or chlorine atom.

The compounds of formula (II) very particularly targeted according to the process of the invention can be categorized into three groups:

(1) the compounds of aliphatic type carrying a double bond and which can be represented by the formula (IIa):

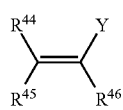

in which:

$R^{44}$, $R^{45}$ and $R^{46}$, which are identical or different, represent a hydrogen atom or a hydrocarbon group having from 1 to 20 carbon atoms which can be a saturated or unsaturated, linear or branched aliphatic group, a saturated, unsaturated or aromatic, monocyclic or polycyclic carbocyclic or heterocyclic group, or any sequence of aliphatic and/or carbocyclic and/or heterocyclic group(s) as mentioned above; and Y symbolizes the leaving group as defined above;

(2) compounds of aliphatic type carrying a triple bond and which can be represented by the formula (IIb):

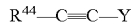

in which:

$R^{44}$ has the meanings given in the formula (IIa); and

Y represents a leaving group as defined above;

(3) compounds of aromatic type which are subsequently denoted by "halogenoaromatic compound" and which can be represented by the formula (IIc):

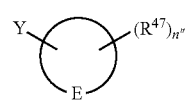

in which:

E symbolizes the residue of a ring forming all or part of a monocyclic or polycyclic aromatic carbocyclic and/or heterocyclic system;

$R^{47}$, which are identical or different, represent substituents on the ring;

Y represents a leaving group as defined above; and n" represents the number of substituents on the ring.

The invention applies to the unsaturated compounds corresponding to the formulae (IIa) and (IIb) in which $R^{44}$ preferably represents a saturated, linear or branched acyclic aliphatic group preferably having from 1 to 12 carbon atoms.

The invention does not rule out the presence of another unsaturated bond in the hydrocarbon chain, such as a triple bond or else one or more double bonds, which can be conjugated or nonconjugated.

The hydrocarbon chain can optionally be interrupted by a heteroatom (for example oxygen or sulfur) or by a functional group, insofar as the latter does not react, and mention may be made in particular of a group such as especially —CO—.

The hydrocarbon chain can optionally carry one or more substituents insofar as they do not react under the reaction conditions and mention may in particular be made of a halogen atom, a nitrile group or a trifluoromethyl group.

The saturated or unsaturated, linear or branched acyclic aliphatic group can optionally carry a cyclic substituent. "Ring" is understood to mean a saturated, unsaturated or aromatic carbocyclic or heterocyclic ring.

The acyclic aliphatic group can be connected to the ring via a valence bond, a heteroatom or a functional group, such as oxy, carbonyl, carboxy, sulfonyl, and the like.

It is possible to envisage, as examples of cyclic substituents, cycloaliphatic, aromatic or heterocyclic substituents, in particular cycloaliphatic substituents comprising 6 carbon atoms in the ring, or benzenic substituents, these cyclic substituents themselves optionally carrying any substituent, insofar as they do not interfere in the reactions occurring in the process of the invention. Mention may in particular be made of alkyl or alkoxy groups having from 1 to 4 carbon atoms.

Among aliphatic groups carrying a cyclic substituent, the aralkyl groups having from 7 to 12 carbon atoms, in particular the benzyl or phenylethyl groups, are more particularly targeted.

In the formulae (IIa) and (IIb), $R^{44}$ can also represent a saturated or unsaturated carbocyclic group preferably having 5 or 6 carbon atoms in the ring, preferably a cyclohexyl group, a saturated or unsaturated heterocyclic group comprising in particular 5 or 6 atoms in the ring, including one or two heteroatoms, such as nitrogen, sulfur and oxygen atoms, a monocyclic aromatic carbocyclic group, preferably a phenyl group, or a fused or nonfused polycyclic aromatic carbocyclic group, preferably a naphthyl group.

With regard to $R^{45}$ and $R^{46}$, they preferably represent a hydrogen atom or an alkyl group having from 1 to 12 carbon atoms, a phenyl group or an aralkyl group having from 7 to 12 carbon atoms, preferably a benzyl group.

In the formulae (IIa) and/or (IIb), $R^{44}$, $R^{45}$ and $R^{46}$ more particularly represent a hydrogen atom or else $R^{44}$ represents a phenyl group and $R^{45}$ and $R^{46}$ represent a hydrogen atom.

It should be noted that $R^{34}$ and $R^{35}$ can also represent a functional group, insofar as they do not interact in the coupling reaction. Mention may be made, as examples of such functional groups, of the amido, ester, ether or cyano groups.

Mention may in particular be made, as examples of compounds corresponding to the formulae (IIa) and (IIb), of vinyl chloride or vinyl bromide, or β-bromo-styrene or β-chlorostyrene, or bromoalkyne or iodoalkyne.

The invention applies in particular to the halogenoaromatic compounds corresponding to the formula (IIc) in which E is the residue of an optionally substituted cyclic compound preferably having at least 4 atoms in the ring, preferably 5 or 6 atoms, and representing at least one of the following rings:

a monocyclic or polycyclic aromatic carbocycle, that is to say a compound composed of at least two aromatic carbocycles which form, with one another, ortho- or ortho- and peri-fused systems or a compound composed of at least two carbocycles, only one of which among them is aromatic, which form, with one another, ortho- or ortho- and peri-fused systems;

a monocyclic aromatic heterocycle comprising at least one of the heteroatoms P, O, N and/or S or a polycyclic aromatic heterocycle, that is to say a compound composed of at least two heterocycles comprising at least one heteroatom in each ring, at least one of the two rings of which is aromatic, which form, with one another, ortho- or ortho- and peri-fused systems, or a compound composed of at least one carbocycle and at least one heterocycle, at least one of the rings of which is aromatic, which form, with one another, ortho- or ortho- and peri-fused systems.

More particularly, the optionally substituted residue E preferably represents the residue of an aromatic carbocycle, such as benzene, of an aromatic bicycle comprising two aromatic carbocycles, such as naphthalene, or of a partially aromatic bicycle comprising two carbocycles, one of the two of which is aromatic, such as 1,2,3,4-tetrahydronaphthalene.

The invention also envisages the fact that E can represent the residue of a heterocycle insofar as it is more electrophilic than the compound corresponding to the formula (Ik).

Mention may be made, as specific examples, of an aromatic heterocycle, such as furan or pyridine, an aromatic bicycle comprising an aromatic carbocycle and an aromatic heterocycle, such as benzofuran or benzo-pyridine, a partially aromatic bicycle comprising an aromatic carbocycle and a heterocycle, such as methylenedioxybenzene, an aromatic bicycle comprising two aromatic heterocycles, such as 1,8-naphthylpyridine, or a partially aromatic bicycle comprising a carbocycle and an aromatic heterocycle, such as 5,6,7,8-tetrahydroquinoline.

In the process of the invention, use is preferably made of a halogenoaromatic compound of formula (IIc) in which E represents an aromatic nucleus, preferably a benzenic or naphthalenic nucleus.

The aromatic compound of formula (IIc) can carry one or more substituents.

In the present text, "more" is understood to mean generally less than four $R^{47}$ substituents on an aromatic nucleus. Reference may be made to the definitions of the $R^{42}$ group in the formula (Ik) for various examples of substituents.

$R^{47}$ can also represent a saturated, unsaturated or aromatic heterocycle comprising 5 or 6 atoms and comprising sulfur, oxygen and/or nitrogen as heteroatom(s). In this respect, mention may in particular be made of the pyrazolyl or imidazolyl groups.

In the formula (IIc), n" is equal to 0, 1, 2, 3 or 4, preferably equal to 1 or 2.

Mention may in particular be made, as examples of compounds corresponding to the formula (IIc), of para-chlorotoluene, para-bromoanisole or para-bromo-trifluorobenzene.

The amount of the compound carrying a leaving group of formula (II), preferably of formula (IIa) or (IIb) or (IIc), employed is generally expressed with respect to the amount of nucleophilic compound and can vary within wide proportions; generally, it is in the vicinity of stoichiometry.

Thus, the ratio of the number of moles of the compound carrying the leaving group to the number of moles of the nucleophilic compound generally varies between 0.1 and 2.0, preferably between 0.5 and 1.5, more preferably between 0.8 and 1.2 and more preferentially between 0.9 and 1.1.

In accordance with the process of the invention, the nucleophilic compound, preferably corresponding to the formulae (Ia) to (Iv), is reacted with a compound carrying a leaving group, preferably corresponding to the formula (II), more preferably to the formulae (IIa) or (IIb) or (IIc), in the presence of an effective amount of a catalytic system comprising a copper/butadienylphosphine complex as defined according to the invention.

This is because it has been discovered that it is possible to carry out coupling reactions, such as defined supra, between nucleophilic compounds and compounds carrying a leaving group by using a catalytic system comprising a copper/butadienylphosphine complex as defined according to the invention.

Mention may be made, as examples of catalytic systems capable of being employed, of those comprising at least one copper/butadienylphosphine complex, such as those defined supra under the generic term Pho-Bu/Cu, that is to say complexes of copper with at least one butadienylphosphine of formula (1) according to the invention.

Mention may be made, as example of complex of Pho-Bu/Cu type particularly suitable for the coupling reactions defined above, of the phenylbutadienyldi-phenylphosphine/copper iodide monomer complex [Ph—CH═CH—CH═CH—PPh$_2$]$_2$CuI, where Ph represents the phenyl radical. As also indicated above, the Pho-Bu/Cu complex can be prepared in situ, in the reaction medium for the coupling reaction.

The total amount of copper/butadienylphosphine complex catalyst employed in the process of the invention, expressed by the molar ratio of the number of moles of complex, expressed as copper, to the number of moles of compound carrying a leaving group, generally varies between 0.001 and 0.5, preferably between 0.01 and 0.1.

According to an alternative form, the invention does not exclude the copper being combined with a small amount of another metal element denoted by M. The metal element M is chosen from Group VIII, Ib and IIb of the Periodic Table of the Elements, as defined above.

Mention may be made, as examples of metals M, of silver, palladium, cobalt, nickel, iron and/or zinc.

Use is advantageously made of a mixture comprising palladium and copper. The palladium can be introduced in the form of a finely divided metal or in the form of an inorganic derivative, such as an oxide or a hydroxide. It is possible to resort to an inorganic salt, preferably nitrate, sulfate, oxysulfate, halide, oxyhalide, silicate or carbonate, or to an organic derivative, preferably cyanide, oxalate, acetylacetonate, alkoxide, more preferably still methoxide or ethoxide, or carboxylate, more preferably still acetate.

It is also possible to employ complexes, in particular chlorine- or cyanide-comprising complexes, of palladium and/or of alkali metals, preferably sodium or potassium, or of ammonium. Mention may in particular be made, as examples of compounds capable of being employed in the preparation of the catalysts of the invention, of palladium(II) bromide, palladium(II) chloride, palladium(II) iodide, palladium(II) cyanide, palladium(II) nitrate hydrate, palladium(II) oxide, palladium(II) sulfate dihydrate, palladium(II) acetate, palladium (II) propionate, palladium(II) butyrate or palladium benzoate.

Mention may be made, as specific examples of nickel derivatives, of nickel(II) halides, such as nickel(II) chloride, bromide or iodide, nickel(II) sulfate, nickel(II) carbonate, salts of organic acids comprising from 1 to 18 carbon atoms, such as, in particular, acetate or propionate, nickel(II) complexes, such as nickel(II) acetylacetonate, di-bromobis(triphenylphosphine)nickel(II) or dibromo-bis(bipyridine)nickel (II), or nickel(0) complexes, such as bis(1,5-cyclooctadiene) nickel(0) or [bis(diphenyl-phosphino)ethane]nickel(0).

Recourse may also be had to derivatives based on iron or on zinc, generally in the oxide or hydroxide form or in the form of salts, such as halides, preferably chloride, nitrates and sulfates.

The amount of the metal element M represents less than 50 mol %, preferably less than 25 mol %, advantageously less than 10 mol %, with respect to the number of moles of copper.

More preferably still, use is made of a catalyst in the form of a complex with a butadienylphosphine comprising only copper.

A base, the function of which is to scavenge the leaving group, is also involved in the process of the invention.

The bases suitable for the process of the invention can be characterized by their pKa, which is advantageously at least greater than or equal to 2, preferably between 4 and 30.

The pKa is defined as the ionic dissociation constant of the acid/base pair when water is used as solvent. Reference may be made, for the choice of a base having a pKa as defined by the invention, inter alia, to the Handbook of Chemistry and Physics, 66$^{th}$ edition, pp. D-161 and D-162.

Mention may be made, among the bases which can be used, inter alia, of inorganic bases, such as carbonates, hydrogencarbonates, phosphates or hydroxides of alkali metals, preferably sodium, potassium or cesium, or of alkaline earth metals, preferably calcium, barium or magnesium.

Recourse may also be had to alkali metal hydrides, preferably sodium hydride, or to alkali metal alkoxides, preferably sodium alkoxides or potassium alkoxides, and more preferably to sodium methoxide, ethoxide or tert-butoxide.

Organic bases, such as tertiary amines, are also suitable and mention may more particularly be made of triethylamine, tri(n-propyl)amine, tri(n-butyl)amine, methyldibutylamine, methyldicyclohexylamine, ethyl-diisopropylamine, N,N-diethylcyclohexylamine, pyridine, 4-(dimethylamino)pyridine, N-methylpiperidine, N-ethyl-piperidine, N-(n-butyl)piperidine, 1,2-dimethyl-piperidine, N-methylpyrrolidine and 1,2-dimethyl-pyrrolidine.

The choice is preferably made, among the bases, of alkali metal carbonates.

The amount of base employed is such that the ratio of the number of moles of base to the number of moles of the compound carrying the leaving group preferentially varies between 1 and 4, preferably in the vicinity of 2.

The coupling reaction, in particular arylation or vinylation or alkynylation reaction, carried out according to the invention is generally carried out in the presence of an organic solvent. Recourse is preferably had to an organic solvent which does not react under the conditions of the reaction.

Recourse is preferably had, as types of solvents employed in the process of the invention, to a polar organic solvent and preferably a polar aprotic organic solvent.

Nonlimiting examples of solvents which can be employed in the process of the invention are chosen from:

linear or cyclic carboxamides, such as N,N-di-methylacetamide (DMAC), N,N-diethylacetamide, dimethyl-formamide (DMF), diethylformamide or 1-methyl-2-pyrrolidinone (NMP);

dimethyl sulfoxide (DMSO);

hexamethylphosphoramide (HMPT);

tetramethylurea;

nitro compounds, such as nitromethane, nitro-ethane, 1-nitropropane, 2-nitropropane and their mixtures, or nitrobenzene;

aliphatic or aromatic nitriles, such as acetonitrile, propionitrile, butanenitrile, isobutanenitrile, pentanenitrile, 2-methylglutaronitrile or adiponitrile;

tetramethylene sulfone (sulfolane);

organic carbonates, such as dimethyl carbonate, diisopropyl carbonate or di(n-butyl) carbonate;

alkyl esters, such as ethyl acetate or isopropyl acetate;

halogenated or nonhalogenated aromatic hydrocarbons, such as chlorobenzene or toluene;

ketones, such as acetone, methyl ethyl ketone, methyl isobutyl ketone, cyclopentanone or cyclohexanone;

nitrogenous heterocycles, such as pyridine, picoline and quinolines.

Use may also be made of a mixture of two or more solvents chosen in particular from those listed above.

The preferred solvents are carboxamides, such as DMF, acetonitrile, DMSO, NMP and DMAC.

The amount of organic solvent to be employed is determined according to the nature of the organic solvent chosen. It is determined so that the concentration of the compound carrying the leaving group in the organic solvent is preferably between 5% and 40% by weight.

According to an alternative form, the nucleophilic compound and/or the compound carrying the leaving group can be used as solvent(s) for the reaction, in which case it is not necessary to add an additional solvent to the reaction medium.

The coupling reaction, that is to say the reaction for the creation of a C—C or C-HE bond according to the process of the invention, is generally carried out at a temperature which is advantageously situated between 0° C. and 200° C., preferably between 20° C. and 170° C. and more preferably still between 25° C. and 140° C.

Said reaction is generally carried out at atmospheric pressure but higher pressures, which can, for example, reach 10 bar, can also be used.

From a practical viewpoint, the reaction is simple to carry out.

The order in which the reactants are employed is not critical. Preferably, the copper/butadienylphosphine complex catalytic system, the nucleophilic compound, preferably of formula (Ia) to (Iv), the base, the compound carrying the leaving group, preferably of formula (II), more preferably of formula (IIa), (IIb) or (IIc), and optionally the organic solvent are charged. The reaction medium is then brought to the desired temperature.

As mentioned above, it is possible, in an alternative form, to introduce the copper and at least one butadienylphosphine as ligand, in order to form the copper/butadienylphosphine complex in situ.

The progress of the reaction is monitored by following the disappearance of the compound carrying the leaving group. At the end of the reaction, a product of the R-Q-R$^0$ type is obtained, R, Q and R$^0$ being as defined above.

The compound obtained is recovered according to the conventional techniques used, in particular by crystallization from an organic solvent.

Mention may in particular be made, as more specific examples of such organic solvents which can be used in the crystallization stage, of aliphatic or aromatic hydrocarbons, which may or may not be halogenated, carboxamides and nitriles. Mention may in particular be made of cyclohexane, toluene, dimethyl-formamide or acetonitrile.

Examples of the implementation of the invention are given below. These examples are given by way of indication, without a limiting nature.

EXAMPLES

Examples A

Syntheses of the Butadienylphosphines

The reactions are carried out under a pure and dry nitrogen atmosphere. 40 ml (2 equivalents, 58.44 mmol) of n-butyllithium (n-BuLi; 1.6 M) are added at −50° C. to a solution of 10 g (29.22 mmol) of dimethyldiphenyl-phosphonium iodide $[Ph_2P(CH_3)_2]^+I^-$ in 300 ml of anhydrous tetrahydrofuran (THF) and then the reaction mixture is brought to −10° C. over one hour (yellow solution). 5.2 ml (1 equivalent, 29.22 mmol) of chlorodiphenyl-phosphine are added at the same temperature. The reaction mixture is left stirring in order to return to ambient temperature over one hour (orange solution) and then one equivalent (or more, if necessary) of the α,β-unsaturated aldehyde is added. The reaction mixture is kept stirred at ambient temperature overnight. The THF is evaporated and then the residue is dissolved in dichloromethane. The organic phase obtained is subsequently washed three times with water, dried over anhydrous magnesium sulfate ($MgSO_4$) and concentrated under vacuum. The products are separated, with satisfactory yields, by chromatography on a silica or alumina column with a mixture of hexane/dichloromethane eluant appropriate for each product.

Example A-1

Cinnamic Butadienylphosphine $Ph(C_4H_4)PPh_2$

The general procedure described above was followed using 4 ml (29.22 mmol) of cinnamaldehyde (trans). The two isomers are separated on an alumina column with a mixture of hexane/dichloromethane (95/5) eluant. The reaction yield is 90% (E/Z=21/79).

Example A-1-1

Cinnamic Butadienylphosphine (Z)-Ph $(C_4H_4)PPh_2$

Identification

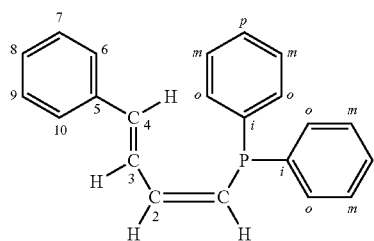

Empirical formula: $C_{22}H_{19}P$
Molecular weight: 314.19
Melting point: 83-86° C. (hexane/dichloromethane)
$^{31}P\{^1H\}$ NMR ($CDCl_3$): δ=−28.08 (s, 1P)
$^1H$ NMR ($CDCl_3$): δ=6.22 (dd, 1H, $H_1$, $^2J_{H1P}$=0.80 Hz); 6.60 (broad d, 1H, $H_4$, $^3J_{H4H3}$=15.26 Hz); 6.97 (quintet, 1H, $H_2$, $^3J_{H2H1}$=11.25 Hz, $^3J_{H2H3}$=11.15 Hz, $^3J_{H2P}$=22.47 Hz); 7.48 (m, 1H, $H_3$, $^4J_{H3H1}$=0.91 Hz, $^3J_{H3H4}$=15.26 Hz, $^4J_{H3P}$=0.0023 Hz), 7.37-7.14 (m, 15H, 3Ph).

$^{13}C\{^1H\}$ NMR ($CDCl_3$): δ=143.96 (d, 1C, $C_2$, $^2J_{CP}$=20.47 Hz); 138.98 (d, 2C, $C_{ips}$, $^1J_{CipsP}$=8.56 Hz); 136.87 (s, 1C, $C_5$); 136.31 (s, 1C, $C_4$); 132.68 (d, 4C, $C_o$, $^2J_{CoP}$=18.98 HZ); 129.70 (d, 4C, $C_3$, $^3J_{C3P}$=13.90 HZ); 128.60 (d, 4C, $C_m$, $^3J_{CmP}$=6.58 Hz); 128.48 (s, 2C, $C_p$, $^4J_{CpP}$=5.12 Hz); 128.14 (s, 2C, $C_{6-10}$); 126.89 (s, 2C, $C_{7-9}$); 126.21 (d, 1C, $C_1$, $^1J_{C1P}$=23.82 Hz).

IR (KBr): ν ($cm^{-1}$)=3020 s, 3010 m, 1620 m, 1570 m, 1470 m, 1430 vs, 1300 w, 1250 w, 1180 m, 1090 s, 1020 s, 980 s, 950 s, 690 vs.

Example A-1-2

Cinnamic Butadienylphosphine (E)-Ph $(C_4H_4)PPh_2$

Identification

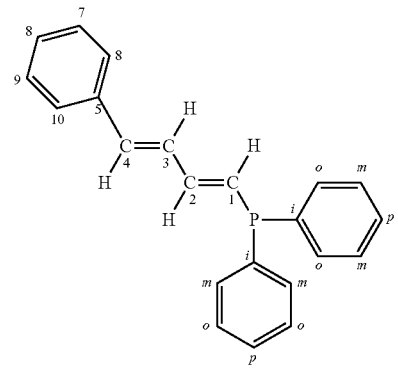 [SMILES: C(/C=C/P(c1ccccc1)c1ccccc1)=C\c1ccccc1]

Empirical formula: $C_{22}H_{19}P$
Molecular weight: 314.19
$^{31}P\{^1H\}$ NMR ($CDCl_3$): δ=−11.32 (s, 1P)
$^1H$ NMR ($CDCl_3$): δ=6.68 (m, 3H, 3CH); 7.45-7.26 (m, 15H, 3Ph); 7.79 (qdd, 1H, CH)

$^{13}C\{^1H\}$ NMR ($CDCl_3$): δ=147.55 (d, 1C, $C_3$, $^3J_{C3P}$=3.52 Hz); 143.74 (d, 1C, $C_2$, $^2J_{CP}$=27.98 Hz); 138.15 (d, 2C, $C_{ips}$, $^1J_{CipsP}$=9.56 Hz); 136.87 (s, 1C, $C_4$); 134.39 (d, 2C, $C_{6-10}$, $^6J_{CP}$=1.46 Hz); 133.18 (d, 4C, $C_o$, $^2J_{CoP}$=19.02 Hz); 129.25 (d, 1C, $C_1$, $^1J_{C1P}$=12.98 Hz); 128.73 (s, 2C, $C_P$); 128.69 (d, 4C, $C_m$, $^3J_{CmP}$=16.40 Hz); 126.70 (s, 2C, $C_{7-9}$); 126.06 (s, 1C, $C_8$).

IR (KBr): ν ($cm^{-1}$)=3040 s, 3010 s, 1640 s, 1580 s, 1470 s, 1430 vs, 1390 w, 1190 s, 1115 s, 1090 m, 1030 m, 980 vs, 850 m, 720 s, 690 vs.

Example A-2

Crotonic Butadienylphosphine $CH_3(C_4H_4)PPh_2$

The general procedure was followed using 2.4 ml (29.22 mmol) of crotonaldehyde (trans-2-butanal). The two isomers are separated on an alumina column with a mixture of hexane/dichloromethane (97/3) eluant. The reaction yield is 80% (E/Z=25/75).

Example A-2-1

Crotonic Butadienylphosphine (Z)—CH$_3$(C$_4$H$_4$)PPh$_2$

Identification:

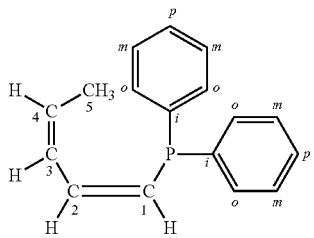 [SMILES: C/C=C\C=C/P(c1ccccc1)c1ccccc1]

Empirical formula: C$_{17}$H$_{17}$P
Molecular weight: 252.14
$^{31}$P{$^1$H} NMR (CDCl$_3$): δ=−28.90 (s, 1P)
$^1$H NMR (CDCl$_3$): δ=1.65 (d, 3H, CH$_3$, $^3J_{H3H4}$=6.62 Hz); 5.73 (m, 1H, H$_3$); 5.94 (dd, 1H, H$_1$, $^3J_{H1H2}$=10.42 Hz, $^3J_{H1P}$=2.02 Hz); 6.79-6.69 (m, 2H, H$_2$ and H$_4$); 7.62-7.11 (m, 10H, 2Ph).
$^{13}$C{$^1$H} NMR (CDCl$_3$): δ=144.60 (d, 1C, C$_2$, $^2J_{C2P}$=21.59 Hz); 139.39 (d, 2C, C$_{ips}$, $^1J_{CipsP}$=8.56 Hz); 134.53 (s, 1C, C$_4$); 132.66 (d, 4C, C$_o$, $^2J_{CoP}$=18.61 Hz); 129.36 (d, 1C, C$_1$, $^1J_{C1P}$=23.82 Hz); 128.53 (d, 4C, C$_m$, $^3J_{CmP}$=6.70 Hz); 128.37 (s, 2C, C$_p$); 126.18 (d, 1C, C$_3$, $^3J_{C3P}$=12.66 Hz); 18.47 (s, 1C, C$_5$).
IR (CCl$_4$): ν (cm$^{-1}$)=3060 s, 3040 s, 3000 s, 2915 s, 1690 vs, 1580 s, 1560 m, 1480 s, 1430 vs, 1370 m, 1300 w, 1100 m, 1030 s, 990 s, 950 s, 930 m, 820 s, 730 vs, 690 vs.

Example A-2-2

Crotonic Butadienylphosphine (E)-CH$_3$(C$_4$H$_4$)PPh$_2$

Identification

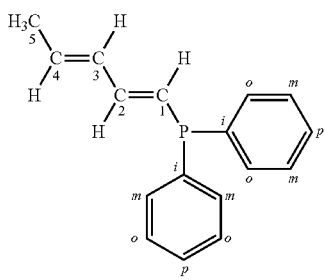 [SMILES: C/C=C/C=C/P(c1ccccc1)c1ccccc1]

Empirical formula: C$_{17}$H$_{17}$P
Molecular weight: 252.14
$^{31}$P{$^1$H} NMR (CDCl$_3$): δ=−12.58 (s, 1P)
$^1$H NMR (CDCl$_3$): δ=1.65 (d, 3H, CH$_3$, $^4J_{H5H3}$=1.51 Hz, $^3J_{H5H4}$=7.07 Hz); 5.80 (sextet, 1H, H$_3$, $^3J_{H3H2}$=10.42 Hz, $^4J_{H3H1}$=6.82 Hz); 6.11 (m, 2H, H$_1$ and H$_4$); 6.47 (m, 1H, H$_2$, $^3J_{H2H1}$=16.27 Hz, $^4J_{H2H4}$=9.60 Hz, $^3J_{H2P}$=1.26 Hz); 7.35-7.14 (m, 10H, 2Ph).
$^{13}$C{$^1$H} NMR (CDCl$_3$): δ=144.88 (d, 1C, C$_2$, $^2J_{CP}$=31.35 Hz); 138.70 (d, 2C, C$_{ips}$, $^1J_{CP}$=9.86 Hz); 132.94 (d, 4C, C$_o$, $^2J_{CP}$=18.82 Hz); 132.56 (s, 1C, C$_4$); 132.39 (d, 1C, C$_1$, $^1J_{CP}$=17.31 Hz); 128.52 (s, 4C, C$_m$); 128.39 (s, 2C, C$_P$); 127.12 (d, 1C, C$_3$, $^3J_{CP}$=9.41 Hz); 18.22 (s, 1C, C$_5$).
IR (CCl$_4$): ν (cm$^{-1}$)=3060 s, 3040 s, 3000 s, 2900 s, 1640 vs, 1580 s, 1475 s, 1430 vs, 1370 m, 1290 m, 1255 w, 1180 w, 1090 s, 1070 s, 1030 vs, 990 vs, 930 w, 690 vs.

Examples B

Preparations of the Copper/Butadienylphosphine Complexes

The butadienylphosphine and the copper salt in the solid form are successively introduced into a Schlenk tube purged three times via vacuum/nitrogen cycles. The reactor is purged under vacuum and then again filled with nitrogen. The solvent (acetonitrile) is then added using a syringe. The reactor is stirred at ambient temperature for 30 min.

When the metal salt is liquid, it is added after the solvent using a syringe.

Example B-1

(Z)-Cinnamic Phosphine/CuI Complex

The general procedure described above was followed using 300 mg (0.954 mmol) of (Z)-cinnamic butadienylphosphine (example A-1-1), 91 mg (0.477 mmol) of cuprous iodide (CuI) and 10 ml of acetonitrile. The white precipitate formed is filtered off and then recrystallized from acetonitrile.

Yield: 383 mg (98%)
Identification:

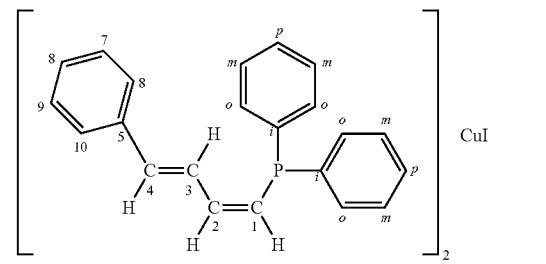

4a(Z)

L = (4-phenyl-1,3-butadienyl)-diphenylphosphine

Iododi{η-[(4-phenyl-1,3-butadienyl)diphenyl-phosphine]}copper complex

Empirical formula: C$_{44}$H$_{38}$CuIP$_2$
Molecular weight: 818.82
Melting point: 200-203° C. (acetonitrile)
$^{31}$P{$^1$H} NMR (CDCl$_3$): δ=−21.86 (s, 1P)
$^1$H NMR (CDCl$_3$): δ=6.03 (dd, 1H, H$_1$, $^3J_{H1H2}$=11.83 Hz, $^2J_{H1P}$=6.36 Hz); 6.47 (d, 1H, H$_4$, $^3J_{H4H3}$=15.26 Hz); 6.83 (quintet, 1H, H$_2$, $^3J_{H2P}$=11.34 Hz); 7.13 (dd, 1H, H$_3$, $^3J_{H2H3}$=11.59 Hz); 7.33-7.18 (m, 15H, 3Ph).
$^{13}$C{$^1$H} NMR (CDCl$_3$): δ=143.70 (d, 1C, C$_2$, $^2J_{CP}$=4.09 Hz); 137.95 (s, 1C, C$_4$); 136.30 (s, 1C, C$_5$); 134.16 (d, 2C, C$_1$, $^1J_{C1P}$=28.66 Hz); 133.29 (d, 4C, C$_o$, $^2J_{CoP}$=13.77 Hz); 129.55 (s, 1C, C$_8$); 128.57 (d, 4C, C$_m$, $^3J_{CmP}$=8.05 Hz);

128.46 (s, 2C, $C_P$); 128.27 (s, 2C, $C_{6-10}$); 127.60 (s, 2C, $C_{7-9}$); 126.15 (d, 1C, $C_3$, $^3J_{C3P}$=13.40 Hz); 123.45 (d, 1C, $C_1$, $^1J_{C1P}$=23.08 Hz).

FAB-MS (positive mode): m/z=691 [(Ph($C_4H_4$)P$Ph_2$)$_2$Cu]$^+$, 377 [(Ph($C_4H_4$)P$Ph_2$)Cu]$^+$.

IR (KBr): ν (cm$^{-1}$)=3066 vw, 3023 vw, 1618 m, 1595 w, 1576 m, 1478 m, 1446 m, 1431 s, 1420 s, 1364 w, 1303 m, 1180 vw, 1156 m, 1096 m, 1066 m, 987 s, 943 s, 755 m, 740 vs, 732 vs, 711 vs, 697 vs, 627 m, 616 w.

X-Ray Structure:

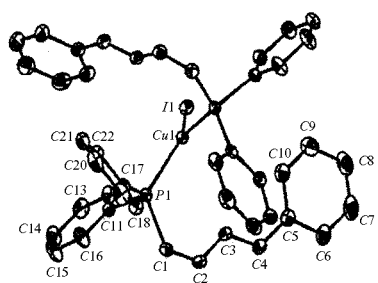

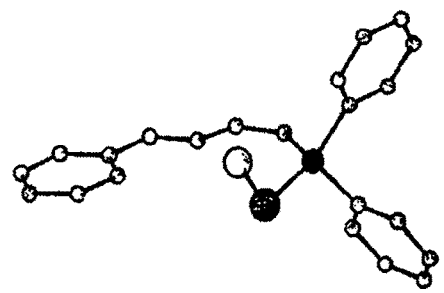

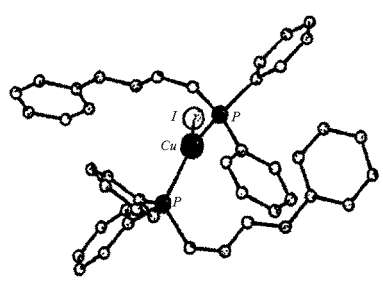

Two phosphine-butadiene ligands are bonded to the copper solely via the doublet of the phosphorus. The double bonds are not involved in the coordination. The third ligand is iodine.

The values of the C1-C2 (1.343 Å) and C3-C4 (1.339 Å) bonds indicate that the double bonds are not involved in the coordination. This is because these values correspond to that of a double bond, diphenylstyryl-phosphine (table below).

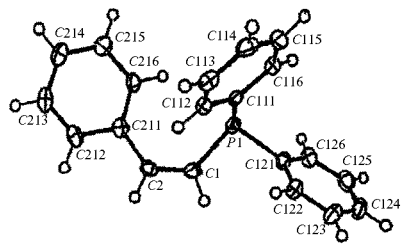

| Bond | Length (Å) |
|---|---|
| C2-C211 | 1.467 (2) |
| C1-C2 | 1.339 (2) |
| P1-C121 | 1.8385 (14) |
| P1-C1 | 1.8412 (15) |
| P1-C1 | 1.8140 (16) |

Example B-2

(Z)-Crotonic Phosphine/CuI Complex

The general procedure described above was followed using 80 mg (0.317 mmol) of (Z)-crotonic butadienylphosphine (example A-2-1), 30 mg (0.158 mmol) of cuprous iodide (CuI) and 5 ml of acetonitrile. After treatment, the residue obtained was dissolved in a minimum amount of dichloromethane and then precipitated from pentane.

Yield: 82 mg (75%).

Identification:

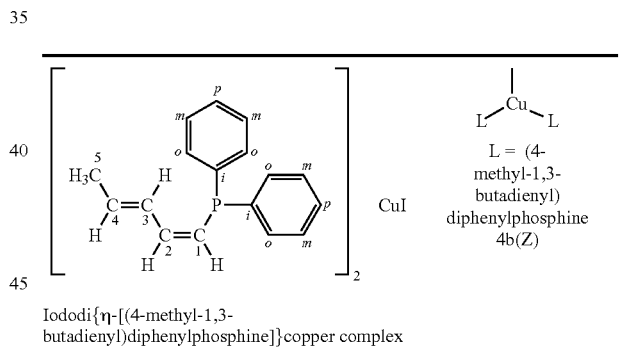

Iododi{η-[(4-methyl-1,3-butadienyl)diphenylphosphine]}copper complex

Empirical formula: $C_{34}H_{34}CuIP_2$
Molecular weight: 694.38
Melting point: 94-96° C. (pentane)
$^{31}P\{^1H\}$ NMR (CDCl$_3$): δ=−23.36 (s, 2P)
$^1H$ NMR (CDCl$_3$): δ=1.61 (d, 6H, 2CH$_3$); 5.98-5.65 (m, 4H, 2H$_1$ and 2H$_3$); 6.97-6.53 (m, 4H, 2H$_2$ and 2H$_4$); 7.35-7.15 (m, 120H, 4Ph).
$^{13}C\{^1H\}$ NMR (CDCl$_3$): δ=18.29 (s, 2C, 2C$_5$); 120.78 (d, 2C, 2C$_1$, $^1J_{C1P}$=21.6 Hz); 128.51 (d, 8C, 8C$_m$, $^3J_{CmP}$=8.9 Hz); 129.35 (s, 4C, 4C$_p$); 129.67 (s, 2C, 2C$_3$); 133.04 (d, 8C, 8C$_o$, $^2J_{CoP}$=14.9 Hz); 134.82 (d, 4C, $^4C_i$, $^1J_{Cip}$=25.7 Hz); 136.55 (s, 2C, 2C$_4$); 144.74 (d, 2C, 2C$_2$, $^2J_{C2P}$=9.7 Hz)

FAB-MS (positive mode): m/z=567 [{CH$_3$(C$_4$H$_4$)PPh$_2$}$_2$Cu]$^+$, 315 [CH$_3$(C$_4$H$_4$)PPh$_2$Cu]

IR (KBr): ν (cm$^{-1}$)=3060 vw, 3000 vw, 2900 vw, 1640 m, 1560 w, 1540 w, 1480 m, 1430 s, 1370 w, 1310 w, 1100 m, 1035 w, 990 s, 950 m, 930 m, 825 w, 750 s, 730 w, 690 vs

Examples C

Acylation Reactions in the Presence of the Butadienylphosphine and a Copper Salt General Procedure The copper salt, the butadienylphosphine (ligand), the nucleophile and the base are successively introduced into a 35 ml Schlenk tube purged three times via vacuum/nitrogen cycles. The arylating agent and then the solvent (acetonitrile) are then added using syringes. The reaction mixture is brought to the desired temperature and stirred at this temperature for the duration shown.

Example C-1

Acylation of Pyrazole

The general procedure described above (solvent: acetonitrile; reaction temperature: 82° C.; duration of the reaction: 12 hours, or 30 hours in the case of bromobenzene) was followed using 9.52 mg (0.05 mmol) of copper iodide CuI, 32 mg (0.1 mmol) of (Z)-cinnamic butadienylphosphine of example A-1-1, 68 mg (0.75 mmol) of pyrazole, 326 mg (1 mmol) of cesium carbonate ($Cs_2CO_3$), 56 μl (0.5 mmol) of iodobenzene (or 53 μl of bromobenzene) and 500 μl of acetonitrile. The oil obtained after treatment (dichloromethane/water extraction) was purified by chromatography on a silica column (eluant: dichloromethane/hexane 50/50).

Yield: 70 mg of colorless oil (98%)
Identification:

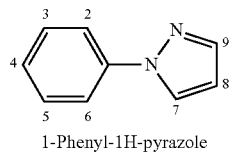

1-Phenyl-1H-pyrazole $^1H$ NMR ($CDCl_3$): δ=7.95-7.96 (dd, 1H, $H_7$); 7.71-7.75 (m, 3H, $H_{2,6,9}$); 7.47-7.50 (m, 2H, $H_{3,5}$); 7.28-7.34 (m, 1H, $H_4$); 6.49-6.50 (dd, 1H, $H_8$).

$^{13}C$ NMR ($CDCl_3$): δ=141.09 ($C_9$); 140.22 ($C_1$); 129.45 ($C_{3,5}$); 126.75 ($C_7$); 126.46 ($C_4$); 119.23 ($C_{2,6}$); 107.61 ($C_8$)

IR (KBr): ν ($cm^{-1}$)=3142; 3050; 2924; 1600; 1520; 1500; 1393; 1332; 1198; 1120; 1046; 936; 914; 755; 689; 654; 610; 515

GC/MS: rt=14.53 min, m/z=144
HRMS: 145.0766 (M+H). Theory: 145.0766

Example C-2

Acylation of 3,5-Dimethylphenol

The general procedure (acetonitrile, 82° C., 12 hours or hours in the case of bromobenzene) was followed using 9.52 mg (0.05 mmol) of copper iodide CuI, 31.4 mg (0.1 mmol) of (Z)-cinnamic butadienylphosphine of example A-1-1, 91.62 mg (0.75 mmol) of 3,5-dimethylphenol, 212 mg (1 mmol) of potassium phosphate ($K_3PO_4$), 56 μl (0.5 mmol) of iodobenzene (53 μl of bromobenzene) and 500 μl of acetonitrile. The oil obtained after treatment (dichloromethane/water extraction) was purified by chromatography on a silica column (eluant: hexane).

Yield: 89 mg of colorless oil (90%)
Identification

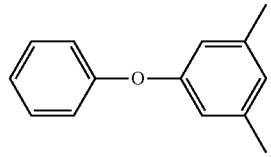

3,5-dimethyldiphenyl ether $^1H$ NMR ($CDCl_3$): δ=7.28-7.42 (m, 2H); 7.12-7.17 (m, 1H); 7.03-7.14 (m, 2H); 6.79 (m, 1H); 6.69 (m, 2H); 2.33 (s, 6H, $CH_3$).

$^{13}C\{^1H\}$ NMR ($CDCl_3$): δ=157.50 (Cq); 157.22 (Cq); 139.61 (2 Cq); 129.70 (2 CH); 125.04 (CH); 123.02 (CH); 118.89 (2 CH); 116.67 (2 CH); 21.35 (2 $CH_3$)

GC/MS: rt=18.24 min, m/z=198
Rf: 0.22 (eluant: hexane)

Example C-3

Arylation of Ethyl Cyanoacetate

Preparation of 2-phenylethyl cyanoacetate

The general procedure (acetonitrile, 82° C., 12 hours with iodobenzene; 30 hours in the case of bromobenzene) was followed using 9.52 mg (0.05 mmol) of copper iodide CuI, 31.4 mg (0.1 mmol) of (Z)-cinnamic butadienylphosphine of example A-1-1, 80 ml (0.75 mmol) of ethyl cyanoacetate, 318 mg (1.5 mmol) of potassium phosphate ($K_3PO_4$), 56 μl (0.5 mmol) of iodobenzene (53 μl of bromobenzene) and 500 μl of acetonitrile. The residue obtained after treatment (dichloromethane/water extraction) was purified by chromatography on a silica column (gradient: hexanes/$CH_2Cl_2$ 100:0 to 75:25).

Yield: 94%
$^1H$ NMR (200 MHz, $CDCl_3$): δ (ppm)=7.37-7.45 (m, 5H); 4.71 (s, 1H); 4.25 (q, $^3J$=7.1 Hz, 2H); 1.28 (t, $^3J$=7.1 Hz, 3H).
$^{13}C\{^1H\}$ NMR (50 MHz, $CDCl_3$): δ (ppm)=165.0 (Cq); 130.0 (Cq); 129.3 (2 CH); 129.2 (2CH); 127.9 (2 CH); 115.7 (CN); 63.3 ($CH_2$); 43.7 (CH); 13.9 ($CH_3$)
GC/MS (EI): rt=15.24 min, m/z: 189
Rf: 0.22 (hexanes/$CH_2Cl_2$ 3:1)

Examples D

Acylation Reactions in the Presence of the (Z)-Cinnamic Phosphine/CuI Complex Obtained in Example B-1

General Procedure

The complex, the base, the nucleophile and the arylating agent are successively introduced into a 35 ml Schlenk tube purged three times via vacuum/nitrogen cycles and then the solvent (acetonitrile) are then added using syringes. The tube is sealed under nitrogen pressure and then stirred and brought to 82° C. for the time shown in the table. After cooling to ambient temperature, the mixture is diluted with dichloromethane (approximately 20 ml) and filtered through Celite (registered brand name). The precipitate is then washed several times with dichloromethane, the filtrate is washed with water, the organic phases are combined and dried over Na$_2$SO$_4$, filtered and concentrated under vacuum, and then the crude products obtained are purified on a chromatography column, elution being carried out with a hexane/dichloromethane mixture.

For a complete characterization of the products obtained, which are all known, see the following papers: arylpyrazoles (Cristau, H. J., Cellier, P. P., Spindler, J.-F.; Taillefer, M., Chemistry, a European Journal, 10, 2004, 5607, or European Journal of Organic Chemistry, 2004, 695), diaryl ethers (ibid, Organic Letters, 6, 2004, 913), vinylpyrazoles and vinyl aryl ethers (Ouali A., Renard B., Spindler, J.-F., Taillefer, M., Chemistry, a European Journal, 2006, 20, 5301).

The reactions carried out are combined in the following table:

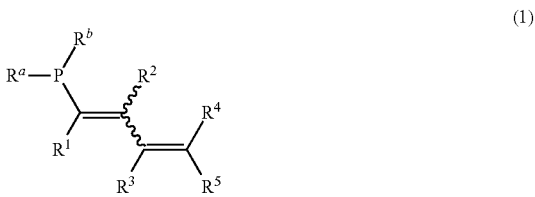

| vinylBr | NuH | Time [h] | Yield [%] |
|---|---|---|---|
| Ph-CH=CH-Br | pyrazole (NH) | 4 | 100 |
| Ph-CH=CH-Br | 3,5-dimethylphenol | 10 | 95 |

What is claimed is:

1. A method for the creation of a carbon-carbon (C—C) bond or of a carbon-heteroatom (C-HE) bond by reacting a compound carrying a leaving group with a nucleophilic compound carrying a carbon atom or a heteroatom (HE) capable of replacing the leaving group, thus creating a C—C or C-HE bond, in which process the reaction is carried out in the presence of an effective amount of a catalytic system comprising at least one copper/butadienylphosphine complex.

2. The method as claimed in claim 1, wherein the copper/butadienylphosphine complex is a complex comprising copper and at least a butadienylphosphine of formula (1):

(1)

in which:
R$^a$ and R$^b$, which are identical or different, each represent a radical chosen independently from alkyl, aryl, heteroaryl, monoalkylamino, dialkylamino, alkoxy, aryloxy and heteroaryloxy;
R$^1$, R$^2$, R$^3$, R$^4$ and R$^5$, which are identical or different, are chosen independently from hydrogen, a hydrocarbon radical, an aryl radical and a heteroaryl radical.

3. The method as claimed in claim 1, in which the R$^a$ and R$^b$ substituents of the butadienylphosphine of formula (1) are identical and each represent a radical chosen independently from alkyl, aryl, heteroaryl, monoalkylamino, dialkylamino, alkoxy, aryloxy and heteroaryloxy.

4. The method as claimed in claim 1, in which the R$^4$ and/or R$^5$ substituents can be connected so as to form, with the carbon atom which carries them, a carbocyclic or heterocyclic group having from 3 to 20 carbon atoms which is saturated, unsaturated, monocyclic or polycyclic, in the latter case comprising two or three rings, it being possible for the adjacent rings to be aromatic in nature.

5. The method as claimed in claim 1, in which the butadienylphosphine of formula (1) is of Z configuration or of E configuration or is in the form of a mixture in all proportions of the Z and E configurations.

6. The method as claimed in claim 1, in which the butadienylphosphine of formula (1) exhibits the following characteristics:
- $R^a$ and $R^b$ are identical and each represent a radical chosen from methyl, ethyl, propyl, butyl, phenyl, naphthyl, pyridyl or quinolyl;
- $R^1$ represents hydrogen, methyl, ethyl or propyl;
- $R^2$, $R^3$ and $R^4$, which are identical or different, are chosen independently from hydrogen, methyl, ethyl and propyl;
- $R^5$ is chosen from hydrogen, methyl, ethyl, propyl, butyl, pentyl, phenyl, naphthyl, pyridyl and quinolyl.

7. The method as claimed in claim 1, in which the butadienylphosphine of formula (1) exhibits the following characteristics:
- $R^a$ and $R^b$ each represent phenyl;
- $R^1$ represents hydrogen;
- $R^2$, $R^3$ and $R^4$, which are identical or different, are chosen independently from hydrogen, methyl, ethyl and propyl;
- $R^5$ is chosen from methyl, ethyl, propyl, phenyl, naphthyl, pyridyl and quinolyl.

8. The method as claimed in claim 1, in which the butadienylphosphine is (Z)-Ph($C_4H_4$)$PPh_2$, (E)-Ph($C_4H_4$)$PPh_2$, (Z)—$CH_3$($C_4H_4$)$PPh_2$ or (E)-$CH_3$Ph ($C_4H_4$)$PPh_2$, where Ph represents phenyl.

9. The method as claimed in claim 1, in which the compound carrying a leaving group is a compound comprising a double bond or a triple bond in the α position with respect to said leaving group or an aromatic compound.

10. The method as claimed in claim 1, in which the nucleophilic compound is an acyclic, cyclic or polycyclic hydrocarbon organic compound comprising at least one atom carrying a free doublet, which may or may not comprise a charge, or comprising a carbon atom which can donate its electron pair.

11. The method as claimed in claim 1, in which the ratio between the number of moles of the compound carrying the leaving group to the number of moles of the nucleophilic compound generally varies between 0.1 and 2.0.

12. The method as claimed in claim 1, in which the total amount of copper/butadienylphosphine complex catalyst, expressed by the molar ratio of the number of moles of complex, expressed as copper, to the number of moles of compound carrying a leaving group, generally varies between 0.001 and 0.5.

13. The method as claimed in claim 1, in which a base having a pKa of between 4 and 30 is involved.

14. The method as claimed in claim 1, in which a base chosen from carbonates, hydrogenocarbonates, phosphates or hydroxides of alkali metals or of alkaline earth metals, alkali metal hydrides, alkali metal alkoxides and tertiary amines is involved.

15. The method as claimed in claim 1, which is carried out in the presence of a polar organic solvent, preferably in the presence of a polar aprotic organic solvent.

16. The method as claimed in claim 1, in which the nucleophilic compound and/or the compound carrying the leaving group is (are) used as solvent(s) for the reaction.

17. The method as claimed in claim 1, in which the copper/butadienylphosphine complex is prepared in situ.

* * * * *